# (12) United States Patent
Casper et al.

(10) Patent No.: US 7,625,752 B2
(45) Date of Patent: Dec. 1, 2009

(54) CELLULAR COMPOSITIONS AND METHODS OF MAKING AND USING THEM

(75) Inventors: Robert Casper, Toronto (CA); Ian Rogers, Toronto (CA)

(73) Assignee: Mount Sinai Hospital, Toronto, Ontario (CA)

( * ) Notice: Subject to any disclaimer, the term of this patent is extended or adjusted under 35 U.S.C. 154(b) by 240 days.

(21) Appl. No.: 10/499,849

(22) PCT Filed: Dec. 20, 2002

(86) PCT No.: PCT/CA02/01979

§ 371 (c)(1),
(2), (4) Date: Nov. 23, 2004

(87) PCT Pub. No.: WO03/055989

PCT Pub. Date: Jul. 10, 2003

(65) Prior Publication Data

US 2005/0074435 A1 Apr. 7, 2005

Related U.S. Application Data

(60) Provisional application No. 60/342,586, filed on Dec. 21, 2001.

(51) Int. Cl.
*C12N 5/00* (2006.01)
(52) U.S. Cl. .................. 435/377; 435/325; 435/375
(58) Field of Classification Search .................. None
See application file for complete search history.

(56) References Cited

U.S. PATENT DOCUMENTS 6,387,367 B1 5/2002 Davis-Sproul et al.

FOREIGN PATENT DOCUMENTS

| WO | WO 98/18486 | 5/1998 |
|---|---|---|
| WO | WO 00/17326 | 3/2000 |
| WO | WO 01/21766 | 3/2001 |
| WO | WO 01/66698 A1 | 9/2001 |
| WO | WO 01/71016 A1 | 9/2001 |

OTHER PUBLICATIONS

Aldskogius H et al. 2002. Strategies for repair of the deafferented spinal cord. Brain Res Rev 40: 301-308.*
Roskams AJ et al. 2005. Directing stem cells and progenitor cells on the stage of spinal cord injury. Exp Neurol 193: 267-272.*
Daley GQ et al. 2003. Realistic prospects for stem cell therapeutics. Hematology 2003: 398-418.*
Kirschstein R. 2001. Can stem cells repair a damaged heart? in Stem Cells: scientific progress and future research directions. pp. 87-92.*
Tosh D et al. 2002. Conversion of pancreatic cells to hepatocytes. Biochem Soc Trans 30: 51-55.*
Castro RF et al. 2002. Failure of bone marrow cells to transdifferentiate into neural cells in vivo. Science 297: 1299.*
Mezey E et al. and Castro RF et al. 2003. "Comment on Failure of bone marrow cells to transdifferentiate into neural cells in vivo", "Response to Comment on Failure of bone marrow cells to transdifferentiate into neural cells in vivo." Science 299:1184b,c.*
Reinecke H et al. 2002. Skeletal muscle stem cells do not transdifferentiate into cardiomyocytes after cardiac grafting. J Mol Cell Cardiol 34: 241-249.*
Murry CE et al. 2004. Hematopoietic stem cells do not transdifferentiate into cardiac mycytes in myocardial infarcts. Nature 428: 664-668.*
Graf T. 2002. Differentiation plasticity of hematopoietic cells. Blood 99: 3089-3101.*
Orkin SH et al. 2002. Hematopoiesis and stem cells: plasticity versus developmental heterogeneity. Nat Immunol 3: 323-328.*
Asahara et al., "Isolation of Putative Progenitor Endothelial Cells for Angiogenesis", Science (1997); 275: 964-967.
Bergstrom et al., "Promoter-Specific Regulation of MyoD Binding and Signal Transduction Cooperate to Pattern Gene Expression", Molecular Cell (2002); 9: 587-600.
Bocci et al., "In-vitro evidence of autocrine secretion of vascular endothelial growth factor by endothelial cells from human placental blood vessels", Molecular Human Reproduction (2001); 7(8): 771-777.
Boiani et al., "Oct4 distribution and level in mouse clones: consequences for pluripotency", Genes & Development (2002); 16: 1209-1219.
Bortvin et al., "Incomplete reactivation of Oct4-related genes in mouse embryos cloned from somatic nuclei", Development (2003); 130: 1673-1680.
Buhring et al., "Stem-cell factor receptor (p145(c-kit)) summary report (CD117)", in Schlosman et al., (eds.), Leucocyte Typing V. Oxford University Press 1995, pp. 1882-1888.
Byrne et al., "Nuclei of Adult Mammalian Somatic Cells Are Directly Reprogrammed to oct-4 Stem Cell Gene Expression by Amphibian Oocytes", Current Biology (2003); 13: 1206-1213.
Byrne et al., "From intestine to muscle: Nuclear reprogramming through defective cloned embryos", PNAS (2002); 99(9): 6059-6063.
Carrera et al., "In vivo response of mouse liver to γ-radiation assessed by the comet assay", Mutation Research (1998); 413: 23-31.

(Continued)

*Primary Examiner*—Lora E Barnhart
(74) *Attorney, Agent, or Firm*—Howson & Howson LLP

(57) ABSTRACT

The invention relates to cellular compositions comprising hematopoietic cells with the potential or increased potential to form non-hematopoietic cells; methods for producing such cellular compositions; methods for differentiation of cells of cellular compositions of the invention into cells that exhibit morphological, physiological, functional, and/or immunological features of non-hematopoietic cells; and uses of the cellular compositions. The invention also relates to a method for the expansion of hematopoietic stem and progenitor cells.

7 Claims, 17 Drawing Sheets

OTHER PUBLICATIONS

Chao et al., "Sustained expression of human factor VIII in mice using a parvovirus-based vector", Blood (2000); 95(5): 1594-1599.

Cosenza et al., "Human Brain Parenchymal Microglia Express CD14 and CD45 and are Productively Infected by HIV-1 in HIV-1 Encephalitis", Brian Pathology (2002); 12: 442-455.

Dao et al., "Reduction in levels of the cyclin-dependent kinase inhibitor $p27^{kip-1}$ coupled with transforming growth factor β neutralization induces cell-cycle entry and increases retroviral transduction of primitive human hematopoietic cells", PNAS (1998); 95: 13006-13011.

Dick, J., "Absence of CD34 on Some Human SCID-Repopulating Cells", Annals New York Academy of Sciences, pp. 211-219.

Dick et al., "Assay of Human Stem Cells by Repopluation of NOD/SCID Mice", Stem Cells (1997); 15: 199-207.

Erices et al., "Human Cord Blood-Derived Mesenchymal Stem Cells Home and Survive in the Marrow of Immunodeficient Mice After Systemic Infusion", Cell Transplantation (2003); 12: 555-561.

Erices et al., "Mesenchymal progenitor cells in human umbilical cord blood", British Journal of Haematology (2000); 109: 235-242.

Gage et al., "Grafting Genetically Modified Cells to the Brian: Possibilities for the Future", Neuroscience (1987); 23(3): 795-807.

Goldfarb, M., "Signaling by Fibroblast Growth Factors: The Inside Story", STKE (2001); 106: PE37.

Gourevitch et al., "Matrix Metalloproteinase Activity Correlates with Blastema Formation in the Regenerating MRL Mouse Ear Hole Model", Developmental Dynamics (2003); 226: 377-387.

Gurdon et al., "Nuclear reprogramming and stem cell creation", PNAS (2003); 100: 11819-11822.

Hakuno et al., "Bone Marrow-Derived Regenerated Cardiomyocytes (CMG Cells) Express Functional Adrenergic and Muscarinic Receptors", Circulation (2002); 105: 380-386.

Hara et al., "Identification of Podocalyxin-like Protein I as a Novel Cell Surface Marker for Hemangioblasts in the Murine Aorta-Gonad-Mesonephros Region", Immunity (1999); 11:567-578.

Hattori et al., "Epigenetic Control of Mouse Oct-4 Gene Expression in Embryonic Stem Cells and Trophoblast Stem Cells", The Journal of Biological Chemistry (2004); 279(17): 17063-17069.

Herger-Katz et al., "The scarless heart and the MRL mouse", Phil. Trans. R. Soc. Lond. B (2004); 3595: 785-793.

Hill et al., "Screening for Novel Pattern Formation Genes Using Gene Trap Approaches", Methods in Enzymology (1993); 225: 664-680.

Hwang et al., "Evidence of a Pluripotent Human Embryonic Stem Cell Line Derived from a Cloned Blastocyst", Science (2004); 303: 1669-1674 (see attachements).

Jiang et al., "Pluripotency of mesenchymal stem cells derived from adult marrow", Nature (2002); 418: 41-49.

Kormori et al., "Targeted Disruption of Cbfal Results in a Complete Lack of Bone Formation owing to Mutational Arrest of Osteoblasts", Cell (1997); 89: 755-764.

Krause et al., "Multi-Organ, Multi-Lineage Engraftment by a Single Bone Marrow-Derived Stem Cell", Cell (2001); 105: 369-377.

Kuwana et al., "Human circulating $CD14^+$ monocytes as a source of progenitors that exhibit mesenchymal cell differentiation", Journal of Leukocyte Biology (2003); 74: 833-845.

Liu et al., "The MyoD-Inducilbe p204 Protein Overcomes the Inhibition of Myoblast Differentiation by ID Proteins", Molecular and Cellular Biology (2002); 2893-2905.

Mareschi et al., "Isolation of human mesenchymal stem cells: bone marrow versus umbilical cord blood", Haematologica (2001); 86: 1099-1100.

Megeney et al., "Severe cardiomyopathy in mice lacking in dystrophin and MyoD", PNAS (1999); 96: 220-225.

Meletis et al., "Have the bloody cells gone to our heads?", The Journal of Cell Biology (2001); 155(5): 699-702.

Mori et al., "DNA base damage generated in vivo in hepatic chromatin of mice upon whole body γ-irradiation", Int. J. Radiat. Biol. (1993); 64(6): 645-650.

Moroni et al., "Fibroblast Growth Factors and Their Receptors in Hematopoiesis and Hematological Tumors", Journal of Hematotherapy & Stem Cell Research (2002); 11: 19-32.

Murray, S., "Letter to the Editor: Induction of Myo D Expression in NIH 3Y3 Cells Produces a Differentiated Myocyte Phenotype without Passing Through a Determination-like State", In Vivo Cell Dev. Biol. (1998); 29A: 446-448.

Murray et al., "Haematopoietic stem cells do not transdifferentiate into cardiac myocytes in myocardial infarcts", Nature (2004); 428: 664-668.

Nakashima et al., "The Novel Zinc Finger-Containing Transcription Factor Osterix is Required for Osteoblast Differentiation and Bone Formation", Cell (2002); 108: 17-29.

Nichols et al., "Formation of Pluripotent Stem Cells in the Mammalian Embryo Depends on the POU Transcription Factor Oct4", Cell (1998); 95: 379-391.

Nielsen et al., "FLT3 Ligand Preserves the Uncommitted $CD34^+CD38^-$ Progenitor Cells During Cytokine Prestimulation for Retroviral Transduction", Journal of Hematotherapy & Stem Cell Research (2000); 9: 695-701.

Ornitz et al., "Ligand Specificity and Heparin Dependence of Fibroblast Growth Factor Receptors 1 and 3", The Journal of Biological Chemistry (1992); 267(23): 16305-16311.

Otto et al., "Cbfal, a Candidate Gene for Cleidocranial Dysplasia Syndrome, Is Essential for Osteoblast Differentiation and Bone Development", Cell (1997); 89: 765-771.

Prockop, D., "Marrow Stromal Cells as Stem Cells for Nonhematopoietic Tissues", Science (1997); 276: 71-74.

Quirici et al., "Isolation of bone marrow mesenchymal stem cells by anti-nerve growth factor receptor antibodies", Experimental Hematology (2002); 30: 783-791.

Sherr et al., "Regulation of CYL/cyclin D genes by colony-stimulation factor I", in Ciba Found Symp. 1992, pp. 209-226.

Stewart et al., "Expression of retroviral vectors in transgenic mice obtained by embryo infection", The EMOB Journal (1987); 6(2): 383-388.

Taswell, C., "Limiting Dilution Assays for the Determination of Immunocompetent Cell Frequencies", The Journal of Immunology (1981); 136(4): 1614-1619.

Taylor, M., "Muscle Differentiation: How Two Cells Become One", Current Biology (2002); 12: R224-R228.

Theise et al., "Derivation of Hepatocytes From Bone Marrow Cells in Mice After Radiation-Induced Myeloablation", Hepatology (2000); 31(1): 235-240.

Theise et al., "Liver from Bone Marrow in Humans", Hepatology (2000); 32(1): 11-16.

Tuli et al., "Characterization of Multipotential Mesenchymal Progenitor Cells Derived from Human Trabecular Bone", Stem Cells (2003); 21: 681-693.

Wakitani et al., "Myogenic cells derived from rat bone marrow mesenchymal stem cells exposed to 5-Azacytidine", Muscle & Nerve (1995); 18: 1417-1426.

Wang et al., "Primitive Human Hematopoietic Cells Are enriched in cord blood compared with adult bone marrow or mobilized peripheral blood as measured by the quantitative in vivo SCID-Repopulating Cell Assay", Blood (1997); 89(11): 3919-3924.

Yamashita et al., "Flkl-positive cells derived from embryonic stem cells serve as vascular progenitors", Nature (2000); 408: 92-96.

"Extensive Amplification and Self-Renewal of Human Primitive Hematopoietic Stem Cells From Cord Blood", Piacibello et al., Blood, vol. 89, No. 8 (Apr. 15), 1997: pp. 2644-2653.

"Hepatocyte Growth Factor Induces Proliferation and Differentiation of Multipotent and Erythroid Hemopoietic Progenitors", Galimi et al., The Rockefeller University Press, 0021-9525/94/12/1743/12, vol. 127, No. 6, Part 1, Dec. 1994: pp. 1743-1754.

Ahmed N, et al 2000, Exp. Hematology 28:1495.

Basilico, C. and D. Moscatelli, Adv. Cancer Re. 59, 115(1992).

Chellaiah et al., 1994, J. Biol. Chem., 269(15):11620-11622.

Dick JE, Ann N Y Acad Sci. Apr. 30, 1999;872:211-7.

Dionne et al., 1990, EMBO J., 9:2685-2692.

Gilliland DG and Griffin JD. Blood Sep. 1, 2002;100(5):1532-42.

Givol and Yayon, 1992, FASEB J., 6:33622269.

Gluckman et al, 1993, N Engl J Med 337, 373-81.

Gothot et al., 1998, Blood 92, 2641-2649.

Gruber et al., 1999, Blood 94, 1077-85.

Heim et al, 1994, Proc. Natl. Acad. Sci. 91:12501.

Huang et al, 1999,Blood 93,2569-2577.
Ladd et al., 1997, Blood 90, 658-68.
Li C, Johnson G, Blood 84; 1994; 408-414.
Madlambayan et al., 2001, J Hematother Stem Cell Res. 10, 481-492.
Matsushime et al, 1991, Cell 65, 701-713.
Merrill et al., 1992, BioEssay 14, 823-830.
Minkin Cedric, Calcif Tissue Int (1982) 34:285-290.
Ogawa, M. 1993, Blood 81, 2844-2853.
Okabe, M. et al, FEBS Letters 407:313-319, 1997.
Petzer et al., 1996, J Exp Med, 183, 2551-2558.
Rao and Kohtz, 1995, J. Biol. Chem, 270, 4093-4100.
Rubenstein et al, 1998, N Engl. J. Med. 339, 1565-77.
Sicinski et al., 1995. Cell, 82, 621-30.
Small et al., 1994, Proc. Natl. Acad. Sci. 91:459-463.
Smith MA, Court EL, Smith JG Blood Rev Dec. 2001;15 (4):191-7.
Piacibello et al, 1999, Blood 93, 3736-49.
Tropepe et al., Dev Biol Apr. 1, 1999;208 (1):166-88.
Tropepe V, et al., 2000, Science 287,pp. 2032.
Van der Putten, 1985, Proc Natl Acad Sci U S A.;82:6148-52.
Yonemura et al, 1996, PNAS 93:4040.
Zernicka-Goetz, M. et al, 1997, Development 124:1133-1137.
Zsebo et al., 1990, Cell 63: 213-224.
Thomas et al, "Purification of hematopoietic stem cells for further biological study", Methods: A Companion to Methods in Enzymology 17:202-218 (Mar. 1999).
Rogers et al, "Identification and analysis of in vitro cultured CD45-positive cells capable of multi-lineage differentiation", Exp. Cell. Res. 313(9):1839-52 (May 15, 2007; e-pub: Mar. 12, 2007).
Rogers and Casper, "Umbilical cord blood stem cells", Best Pract. Res. Clin. Obstet. Gynaecol. 18(6):893-908 (Dec. 2004).
Examination Report dated Nov. 28, 2006 issued in counterpart European Patent Application No. 02784995.9.
Examination Report dated Jul. 9, 2007 issued in counterpart European Patent Application No. 02784995.9.
Bennett, "Cooperative Interactions Between RB and p53 Regulate Cell Proliferation, Cell Senescence, and Apoptosis in Human Vascular Smooth Muscle Cells From Atherosclerotic Plaques" Circulation research, vol. 82, No. 6 (Apr. 6, 1998) pp. 704-712.
Bicknese, "Human Umbilical Cord Blood Cells Can Be Induced to Express Markers for Neurons and Glia" Cell Transplantation, vol. 11, (No. 3, 2002) pp. 261-264.
Chua, "Neural Progenitors, Neurons And Oligodendrocytes From Human Umbilical Cord Blood Cells In A Serum-Free, Feeder-Free Cell Cultuer", Biochemical and Biophysical Research Communications, vol. 379, No. 2 (Feb. 6, 2009: EpubDec. 25, 2008) pp. 217-221.
Gallacher, "Isolation and Characterization of Human CD34(-)Lin(-) and CD34(+)Lin(-) Hematopoietic Stem Cells Using Cell Surface Markers AC133 and CD7", Blood, vol. 95, No. 9 (May 1, 2000) pp. 2813-2820.
Goodwin, "Multilineage Differentiation Activity by Cells Isolated From Umbilical Cord Blood: Expression of Bone, Fat, and Neural Markers", Biology of Blood and Marrow Transplantation, vol. 7 (Nov. 2001) pp. 581-588.
Khademhosseini, "In Vitro Differentiation of Bone Marrow Derived Lin CD45 SCA-1 c-kit Cells into Hepatocyte-Like Cells", 2001 Annual Meeting Abstracts, Blood, vol. 98, No. 11, part 1, Abstract #2293 (Nov. 16, 2001) pp. 548a.
Miller, "Chimerism in Embryos and Adults Following the Injection of Mouse and Human Hematopoietic and Mouse Neural Stem Cells into Mouse Blastocysts" 2000 Annual Meeting Abstracts, Blood, vol. 96, No. 11, part 1, Abstract #1184 (Nov. 16, 2000) pp. 276a.
Madlambayan, "Clinically Relevant Expansion of Hematopoietic Stem Cells With Conserved Function in a Single-use, Closed-system Bioprocess" Biology of Blood and Marrow Transplant, vol. 12, No. 10 (Oct. 2006) pp. 1020-1030.
Orlic, "Bone Marrow Cells Regenerate Infarcted Myocardium", Nature, vol. 410 (Apr. 5, 2001) pp. 701-705.
Piacibello, "Ex Vivo Expansion of Cord Blood Progenitors", Vox Sanguinis, vol. 74 Supplemental 2 (Jun. 1998) pp. 457-462.
Qiu, "Ex Vivo Expansion of CD34+ Umbilical Cord Blood Cells in a Defined Serum-Free Medium (QBSF-60) with Early Effect Cytokines" Journal of Hematotherapy & Stem Cell Research, vol. 8, No. 6 (Dec. 1999) pp. 609-618.
Rogers, "Stem Cells: You Can't Tell a Cell by Its Cover", Human Reproduction Update, vol. 9, No. 1 (Jan.-Feb. 2003) pp. 25-33.
Rogers, "A Simplified Procedure for Hematopoietic Stem Cell Amplification Using A Serum-Free, Feeder Cell-Free Culture System", Biology of Blood and Marrow Transplant, vol. 14, No. 8 (Aug. 2008) pp. 927-937.
Shah, "Flt3 Ligand Induces Proliferation of Quiescent Human Bone Marrow CD34+CD38− Cells And Maintains Progenitor Cells In Vitro", Blood, vol. 87, No. 9 (May 1, 1996) pp. 3563-3570.
Storms, "Hoechst Dye Efflux Reveals A Novel CD7(+)CD34(−) lymphoid Progenitor In Human Umbilical Cord Blood", Blood, vol. 96, No. 6 (Sep. 15, 2000) pp. 2125-2133.
Sanchez-Ramos, "Expression of Neural Markers in Human Umbilical Cord Blood", Experimental Neurology, vol. 171, No. 1 (Sep. 2001) pp. 109-115.
Ueda, "Expansion Of Human NOD/SCID-Repopulating Cells By Stem Cell Factor, Flk2/Flt3 ligand, thrombopoietin, IL-6, And Soluble IL-6 Receptor", Journal of Clinical Investigation, vol. 105, No. 7 (Apr. 2000) pp. 1013-1021.
Van Hennik, "Highly Efficient Transduction of the Green Fluorescent Protein Gene in Human Umbilical Cord Blood Stem Cells Capable of Cobblestone Formation in Long-Term Cultures and Multilineage Engraftment of Immunodeficient Mice", Blood, vol. 92 No. 11 (Dec. 1, 1998) pp. 4013-4022.
Zigova, "Human Umbilical Cord Blood Cells Express Neural Antigens After Transplantation Into the Developing Rat Brain", Cell Transplantation, vol. 11, No. 3, (2002) pp. 265-274.
Zulli, "Embryonic Stem Cells Markers Are Present Within Rabbit Atherosclerotic Plaques", Histology and Histopathology, vol. 23, No. 6 (Jun. 2008) pp. 741-746.
EP 02 784 995.9 - 2403 Examination Report (May 16, 2008).
JP 2003-556509 Notice of Reasons for Rejection (Aug. 22, 2008).
IL 162648 Office Action (May 29, 2008).
AU 2002350352 Office Action (Jan. 29, 2007).
SG 200305170-3 (Patent No. 1000111) Examination Report (Apr. 22, 2006).
SG 200305170-3 (Patent No. 1000111) Invitation to Respond to Written Opinion (Sep. 14, 2004).
SG 200305170-3 (Patent No. 1000111) Invitation to Respond to Written Opinion (May 10, 2005).
Response to EP 02 784 995.9 - 2403 Examination Report by Applicant (Nov. 13, 2008).

* cited by examiner

Lin- Cells

Control     IgG

Day 0     CD45

HLA-ABC

Day 7     CD45

HLA-ABC

GM-CSF/ NO SERUM

GM-CSF/ + SERUM

MYO D

MUSCLE ACTIN

Glial Fibrillary Acidic Protein (GFAP)

Neat    1/10    1/100    Genomic Control

NESTIN (neural)

UBC- Neural Marker Positive

POSITIVE ADIPOCYTES

CELLULAR COMPOSITIONS AND METHODS OF MAKING AND USING THEM

FIELD OF THE INVENTION

The invention relates to cellular compositions comprising hematopoietic cells with the potential or increased potential to form non-hematopoietic cells; methods for producing such cellular compositions; methods for differentiation of cells of cellular compositions of the invention into cells that exhibit morphological, physiological, functional, and/or immunological features of non-hematopoietic cells; and uses of the cellular compositions. The invention also relates to a method for the expansion of hematopoietic stem and progenitor cells.

BACKGROUND OF THE INVENTION

Organ transplantation has been successfully used to replace or repair damaged tissues. However, transplantation is limited by the availability of donors, and the high costs and radical nature of the surgery. It is evident that alternative procedures to transplantation are desirable.

The grafting of healthy cells into diseased tissue has been proposed as an alternative to organ transplantation. However, the success of such grafts is dependent upon the developmental stage of the injected cells. Adult cells generally do not incorporate into tissue but early stage embryonic cells stably integrate. Embryonic cell grafts are not preferred due to the ethical issues involved, and technical and availability limitations. Thus, there is a need for alternative sources of cells capable of integration into tissues. In particular, a need exists for cell preparations containing cells of various tissues for transplantation in which (1) the preparation is accepted by the patient, thus avoiding the difficulties associated with immunosuppression, (2) the preparation is safe and effective, thus justifying the cost and effort associated with treatment, and (3) the preparation is efficacious during and after transplantation.

Bone marrow transplantation is a common form of therapy for a number of diseases involving dysfunction of hematopoietic cells, or which involve treatments which irreversibly damage hematopoietic cells (e.g. chemotherapy and radiotherapy for cancer). The use of bone marrow transplantation has allowed more intensive and effective chemotherapy and radiotherapy for cancer. However, the approach requires an adequate number of stem cells to ensure success. Thus, there is a need for sources of hematopoietic stem cells that will reduce the risk of graft versus host rejection and provide an adequate number of stem cells for transplantation.

The citation of any reference herein is not an admission that such reference is available as prior art to the instant invention.

SUMMARY OF THE INVENTION

The present inventors have identified distinct cells that can differentiate into cells of multiple tissue types in vivo and in vitro. The cells were produced by growing hematopoietic cells derived from umbilical cord blood under selected proliferation conditions. The cells have properties similar to embryonic stem cells.

The inventors have also developed a method for the expansion of hematopoietic stem and progenitor cells from umbilical cord blood that provides a significant increase in the number of hematopoietic stem cells and progenitor cells available for transplant from a single umbilical cord. A single umbilical cord yields enough stem cells for one bone marrow transplant, typically for a pediatric patient. In vitro expansion of the stem cells will increase the possible uses for a single cord blood collection. Stem cell expansion will allow greater accessibility to this form of treatment and allow for the development of cord blood stem cells for gene therapy. In addition, the degree of HLA incompatibility that can be tolerated is greater with cord blood than with bone marrow (1). This is important to the establishment of cord blood banks because it increases the donor pool.

Thus, an aspect of the present invention is directed to methods of producing cells with potential or increased potential to form different types of non-hematopojetic cells. In accordance with the present invention, the method begins with obtaining hematopoietic cells (e.g. from umbilical cord blood) and enriching the cells for hematopoietic stem cells and progenitor cells by positive or negative selection. The resulting cell preparation enriched for hematopoictic stem cells and progenitor cells is cultured under proliferation conditions to produce cells with potential or an increased potential to form different types of non-hematopoietic cells. This novel process leads to the preparation of hematopoietic cells with the potential or increased potential to form different types of non-hematopoietic cells in vitro and in vivo.

In an embodiment, a cellular composition is provided comprising cells with the potential or increased potential to form non-hematopoietic cells produced by a method of the invention, in combination with an effective amount of at least one differentiation factor.

In an embodiment, a method is provided for converting hematopoietic cells into cells with potential or increased potential to form different types of non-hematopoietic cells. The method of converting hematopoietic cells into newly created cells with potential or increased potential to form non-hematopoietic cells involves obtaining hematopoietic cells (e.g. from umbilical cord blood) and enriching the cells for hematopoietic stem cells and progenitor cells by positive or negative selection; and culturing the resulting cell preparation under proliferation conditions so that cells in the preparation develop the potential or an increased potential to form different types of non-hematopoietic cells and tissues.

Another aspect of the invention is an enriched hematopoietic cell preparation that is enriched for hematopoietic stem cells and progenitor cells that are capable of forming cells that have the potential or increased potential to form cells of multiple tissue types both in vitro and in vivo. In an embodiment, the enriched hematopoietic cell preparation comprises essentially CD45$^+$HLA-ABC$^+$ cells (HLA-Class 1+), preferably CD45$^+$HLA-ABC$^+$Lin$^-$.

In another aspect the invention relates to an isolated cellular composition comprising or comprising essentially cells with the potential or increased potential to form hematopoietic and non-hematopoietic cells in vitro and in vivo. The cells in the composition may have an altered differentiation program enabling the cells to form non-hematopoietic cells. The cells have the potential to differentiate into cells that exhibit morphological, physiological, functional, and/or immunological features of non-hematopoietic cells. The cells may be further characterized by embryonic or early non-hematopoietic tissue markers (e.g. early muscle marker Desmin).

In an embodiment, a cellular composition is provided comprising essentially cells with the potential or increased potential to form different types of non-hematopoietic cells produced by a method of the invention.

In a particular aspect of the invention, a cellular composition is provided which is produced by culturing hematopoietic cells comprising hematopoietic stem cells and progenitor cells, preferably an enriched hematopoietic cell preparation comprising CD45⁺HLA-ABC⁺ cells, more preferably comprising CD45⁺HLA-ABC⁺Lin⁻ cells, under proliferation conditions and isolating cells in the culture that have the potential or increased potential to form different types of non-hematopoietic cells and hematopoietic cells both in vitro and in vivo.

Cells with the potential or increased potential to form non-hematopoietic cells in a cellular composition may be induced to differentiate into cells and tissues of different types of non-hematopoietic lineages in vitro or in vivo. Thus, the invention relates to methods of isolating a population of essentially non-heinatopoietic cells from hematopoietic cells with the potential or increased potential to form non-hematopoietic cells produced by a method of the invention.

The invention therefore also relates to a purified cellular composition comprising or comprising essentially cells with potential or increased potential to form different types of non-hematopoietic cells that have been induced to differentiate into cells of non-hematopoietic cell lineages, preferably cells that exhibit morphological, physiological, functional, and/or immunological features of non-hematopoietic cells. A differentiated cell preparation is characterized by expression of genetic markers of non-hematopoietic cell lineages (e.g. markers for muscle, neural, adipocyte, osteoclast, osteoblast, endothelial, astrocytes, renal, retinal, cornea, and hepatocyte lineages).

In an embodiment, a cellular composition is provided comprising cells with the potential or increased potential to form non-hematopoietio cells produced by a method of the invention, in combination with an effective amount of at least one differentiation factor.

In another embodiment, a cellular composition is provided comprising mitotic or differentiated cells that are progeny of cells with the potential or increased potential to form non-hematopoietic cells produced by a method of the invention.

In an aspect the invention provides a culture system comprising cells, cell preparations, and cellular compositions of the invention.

The invention also contemplates cells, cell preparations, and cellular compositions of the invention in combination with a substrate or matrix, preferably a substrate or matrix adapted for transplantation into a patient The substrate may be an engineered biomaterial or porous tissue culture insert.

The present invention also provides a method for expanding, preferably selectively expanding, hematopoietic stem cells and progenitor cells from umbilical cord blood. The method comprises (a) culturing an enrichedhematopoietic cell preparation from umbilical cord blood comprising hematopoietic stem cells and progenitor cells under proliferation conditions; and (b) isolating increased numbers of hematopoietic stem cells and progenitor cells. "Increased numbers of hematopoietic stem cells and progenitor cells", refers to an increase in the number of cells by at least about 2-fold relative to the number of hematopoietic stem cells and progenitor cells that are present in a parallel control culture of cells that are not subjected to the same proliferation conditions. The invention also relates to an expanded hematopoietic stem cell and progenitor cell preparation obtained by this method The term "expanding" or "expansion" contemplates the proliferation of the hematopoietic cells.

In an embodiment the invention provides a method for expanding hematopoietic stem cells and progenitor cells comprising (a) obtaining umbilical cord blood and enriching for hematopoietic stem cells and progenitor cells by positive or negative selection, preferably enriching for CD45⁺HLA-ABC⁺ cells, more preferably CD45⁺HLA-ABC⁺Lin⁻ cells; (b) culturing the resulting enriched hematopoietic cell preparation under proliferation conditions; and (c) isolating increased numbers of hematopoietic stem cells and progenitor cells.

In an aspect the invention provides a method of identifying the presence of cells of cell preparations and cellular compositions of the invention in a mixed cell population comprising: exposing the cell population to an antibody or fragment thereof immunogenetically specific for a marker of such cells, the occurrence of the markers being indicative of the presence of the cells in the cell population. The antibody may comprise a detectable label. The method may involve a selection step involving fluorescence-activated cell sorting or magnetic bead separation. In an embodiment, the mixed cell population is contacted with one, two, three, four, five, six, seven, eight, nine, ten, or eleven or more, preferably all, of the following markers CD45, HLA-ABC, stem cell factor receptor, Flt3ligand receptor, Fgf receptor, an embryonic stem cell protein such as Oct4, Stage Specific Embryonic Antigen-3 (SSEA3), and/or Stage Specific EmbryonicAntigen-4 (SSEA4), HoxB4, Flk-1, CD34, and CD38. This method of identifying cells may have diagnostic applications in diseases or disorders involving cells of the present invention. The method may be employed in the diagnosis of early childhood cancers, stem-cell based cancers, and endogenous stem-cell assessment in patients. The method may also be used to monitor a therapy for diseases or disorders associated with or involving cells of the present invention.

Cells, cell preparations, and cellular compositions of the invention can be used in a variety of methods (e.g. transplantation or grafting) and they have numerous uses in the field of medicine. Cells with the potential or increased potential to form non-hematopoietic cells, or cells differentiated there from may be used for the replacement of body tissues, organs, components or structures which are missing or damaged due to trauma, age, metabolic or toxic injury, disease, idiopathic loss, or any other cause.

In an aspect of the invention, the newly created cellular compositions comprising cells with potential or increased potential to form non-hematopoietic cells, or non-hematopoietic cells differentiated therefrom, can be used in both cell therapies and gene therapies aimed at alleviating disorders and diseases involving the non-hematopoietic cells. The invention obviates the need for human tissue to be used in various medical and research applications.

The invention also provides a method of treating a patient with a condition involving a non-hematopoietic cell, in particular a defect in a non-hematopoietic cell, comprising transferring or administering an effective amount of a cellular composition comprising cells with the potential to form the non-hematopoietic cells into the patient, wherein the cells differentiate into the non-hematopoietic cells.

The invention also contemplates a cell line comprising cells with the potential or increased potential to form non-hematopoietic cells produced by a method of the invention that have the ability to migrate and localize to specific regions in a patient where they differentiate into non-hematopoietic cells typical of the region and they integrate into the tissue in a characteristic tissue pattern.

Expanded hematopoietic stem cell and progenitor cell preparations of the invention may be used in both cell therapies and gene therapies aimed at alleviating disorders and diseases involving hematopoietic cells. The invention contemplates a method of treating a patient with a condition involving hematopoietic cells comprising transferring to a patient an effective amount of a cell preparation of the invention comprising hematopoietic stem cells and progenitor cells.

Cells with the potential or increased potential to form non-hematopoietic cells may be used to screen for potential therapeutics that modulate development or activity of such cells or cells differentiated therefrom.

The cells, cell preparations, and cellular compositions of the invention may be used as immunogens that are administered to a heterologous recipient The cells, cell preparations, and cellular compositions of the invention may be used to prepare model systems of disease. The cells, cell preparations, and cellular compositions of the invention can also be used to produce growth factors, hormones, etc.

The invention also contemplates a pharmaceutical composition comprising cells, a cell preparation, or cellular composition of the invention, and a pharmaceutically acceptable carrier, excipient, or diluent. A pharmaceutical composition may include a targeting agent to target cells to particular tissues or organs.

The invention provides a method for obtaining non-hematopoietic cells for autologous transplantation from a patient's own hematopoietic cells comprising (a) obtaining a sample comprising hematopoietic cells from the patient, preferably from fresh or cryopreserved umbilical cord blood; (b) separating out an enriched cell preparation comprising hematopoietic stem cells and hematopoietic progenitor cells, preferably $CD45^+HLA-ABC^+$ cells, more preferably $CD^{45+}$ $HLA-ABC^+Lin^-$ cells; (b) culturing the cells under proliferation conditions to produce a cellular composition comprising cells with the potential or increased potential to form non-hematopoietic cells.

The invention also relates to a method for conducting a regenerative medicine business. Still further the invention relates to a method for conducting a stem cell business involving identifying agents which affect the proliferation, differentiation, function, or survival of cells that have the potential to form hematopoietic and non-hematopoietic cells of the invention. An identified agent(s) can be formulated as a pharmaceutical preparation, and manufactured, marketed, and distributed for sale.

In another aspect, the invention contemplates methods for influencing the proliferation, differentiation, or survival of cells that have the potential to form hematopoietic and non-hematopoietic cells by contacting cells of a cellular composition of the invention with an agent or agents identified by a method of the invention.

The invention also contemplates a method of treating a patient comprising administering an effective amount of an agent-identified in accordance with a method of the invention to a patient with a disorder affecting the proliferation, differentiation, function, or survival of hematopoietic or non-hematopoietic cells.

The invention also contemplates a method for conducting a drug discovery business comprising identifying factors or agents that influence the proliferation, differentiation, function, or survival of cells that have the potential to form hematopoietic and non-hematopoietic cells of the invention, and licensing the rights for further development.

The invention further contemplates a method of providing drug development wherein a cellular composition of the invention or mitotic or differentiated progeny thereof are used as a source of biological components of non-hematopoietic or hematopoietic cells in which one or more of these biological components are the targets of the drugs that are being developed.

The invention also relates to methods of providing a bioassay.

In an aspect, the invention features a kit including cells generated using a method of the invention, or a mitotic or differentiated cell that is the progeny of the cells.

The invention is also directed to a kit for transplantation of non-hematopoietic cells comprising a flask with medium and cells, a cell preparation, or a cellular composition of the invention.

The invention also relates to a method of using the cellular compositions in rational drug design.

In an aspect, the invention relates to a kit for rational drug design comprising non-hematopoietic cells obtained by a process of the invention. In an embodiment, the kit comprises hepatocytes and instructions for their use in toxicity assays. In another embodiment, the kit comprises intestinal cells and instructions for their use in an absorption assay.

Still another aspect of the invention is a kit for producing cellular compositions comprising cells that have the potential or increased potential to form cells capable of differentiating into cells of multiple tissue types both in vitro and in vivo, or for producing an expanded hematopoietic stem cell and progenitor cell preparation.

DESCRIPTION OF THE DRAWINGS

The invention will now be described in relation to the drawings in which.

Figure 9:
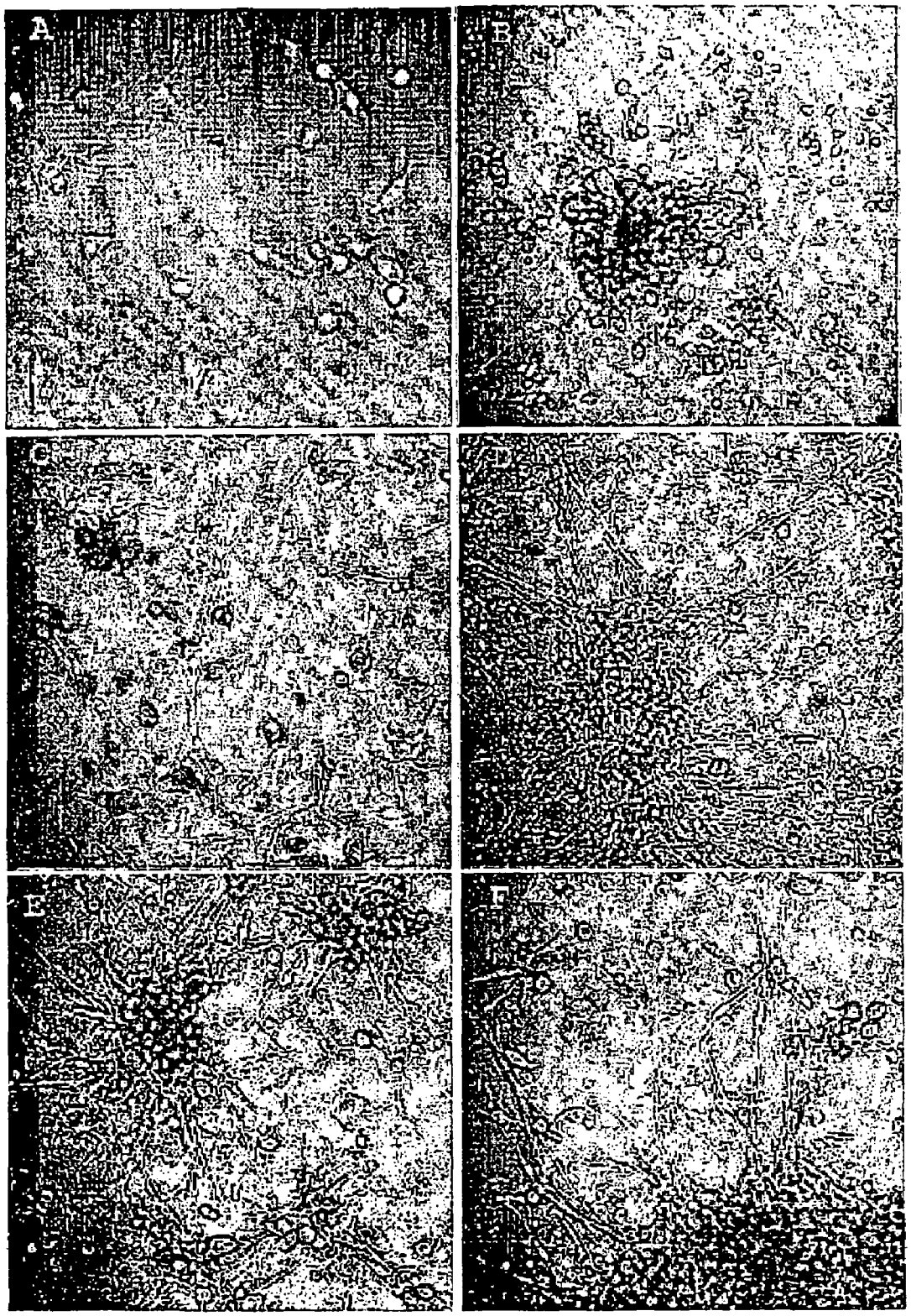

FIG. 9 shows endothelial cells. Lin⁻ cells are positive for Flk-1 after growth in Fgf, SCF, FLT3 ligand conditions. When these cells are grown in the presence of VEGF the cells elongate and lose Flk-1 as expected for endothelial cell development (A). The same cells placed in a matrix will grow into a network of vessel like structures B-F).

Figure 10:
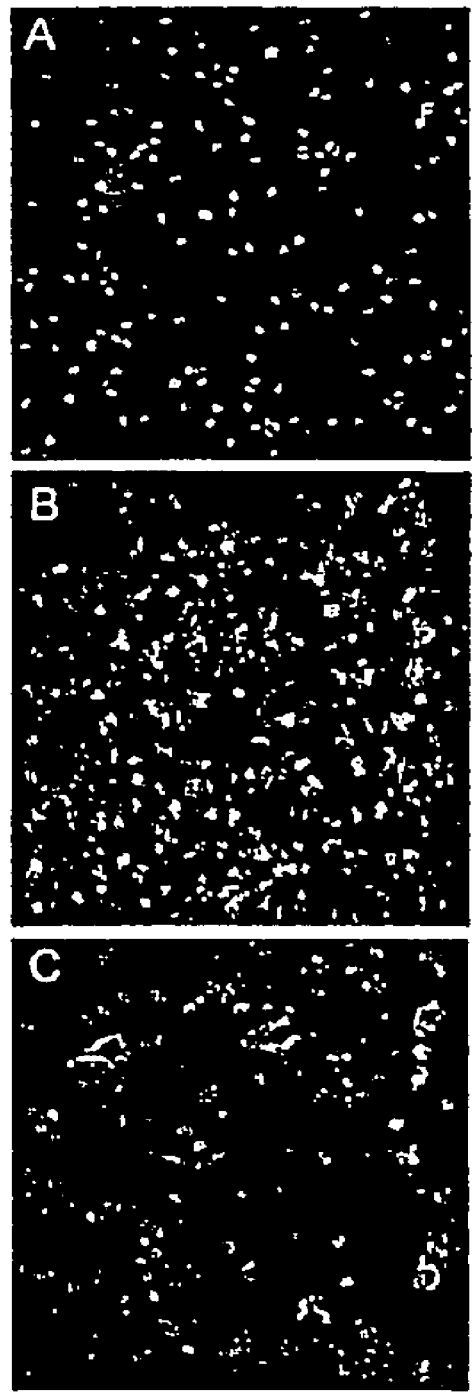

FIG. 10 shows CD31 positive endothelial cells. High numbers of CD31 positive cells can be obtained from UCB Lin– cells. Cells were grown in conditions described herein and stained using an IgG control (A), and an anti-CD31 antibody (B and C).

Figure 11:
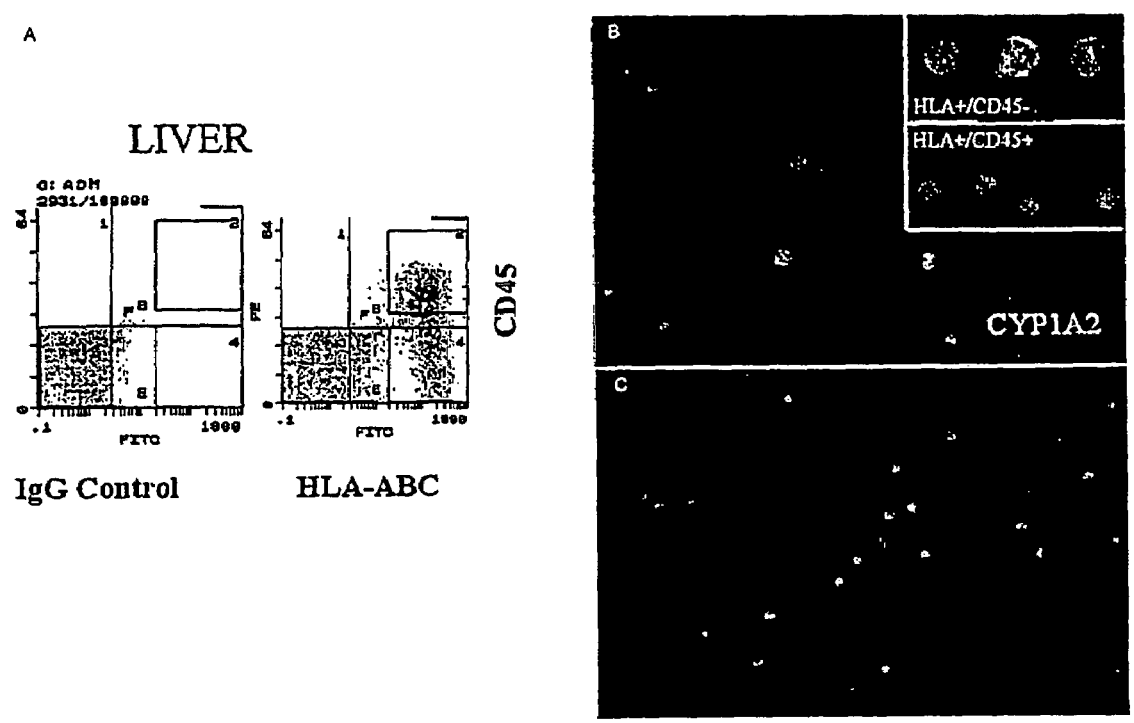

FIG. 11 shows hepatocytes from UCB cells. CYP1A2 positive hepatocytes were found in the livers of NOD/SCID mice engrafted with human UCB Lin⁻ cells. Human, non-blood cells (CD45⁻/HLA⁺) were isolated from engrafted mouse livers by flow cytometry (A). Both CD45⁺/HLA⁺ human blood cells and the human, non-blood cells were tested for the presence of CYP1A2 (B&C). CYP1A2 positive cells represent a functional hepatocyte. These cells are fewer in number than the total number of human, non-blood cells found in the liver. None of the mouse cells or the human blood cells express CYP1A2.

Figure 12:

FIG. 12 shows the immunohistochemistry of engrafted mouse livers. immunohistochemistry on liver sections with CYP1A2 antibody was done. Positive cells were detected.

Figure 13:
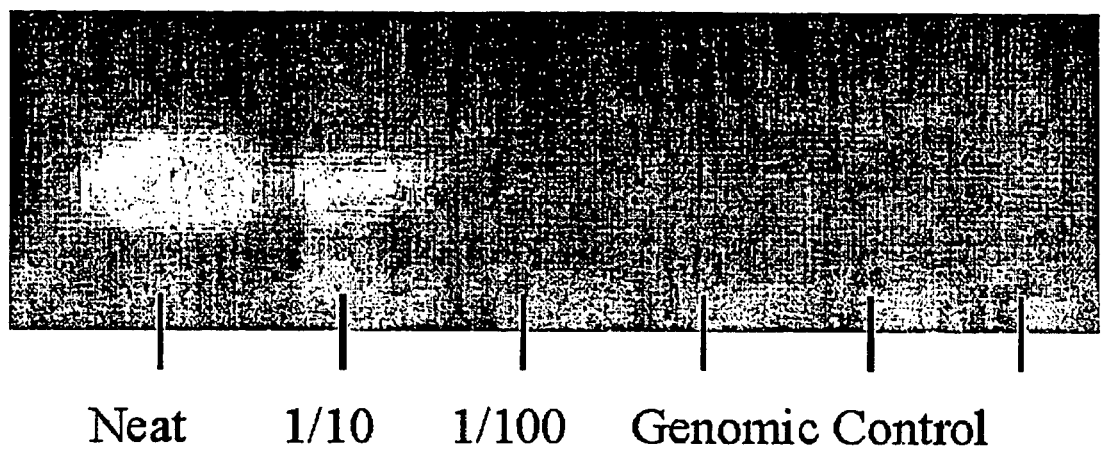

FIG. 13 shows astrocytes detected in the Lin⁻ population. Lin⁻ cells are negative for the astrocyte marker GFAP unless first grown in Fgf, SCF, FL3 ligand. PCR was used to detect the presence of GFAP mRNA.

Figure 14:
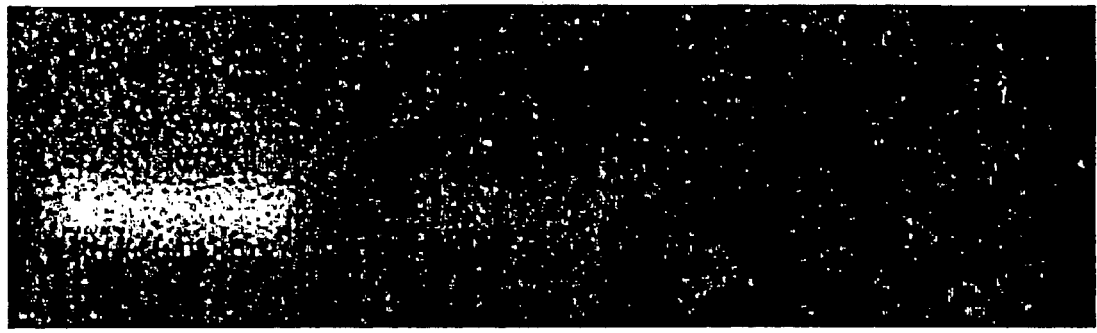
Figure 15:
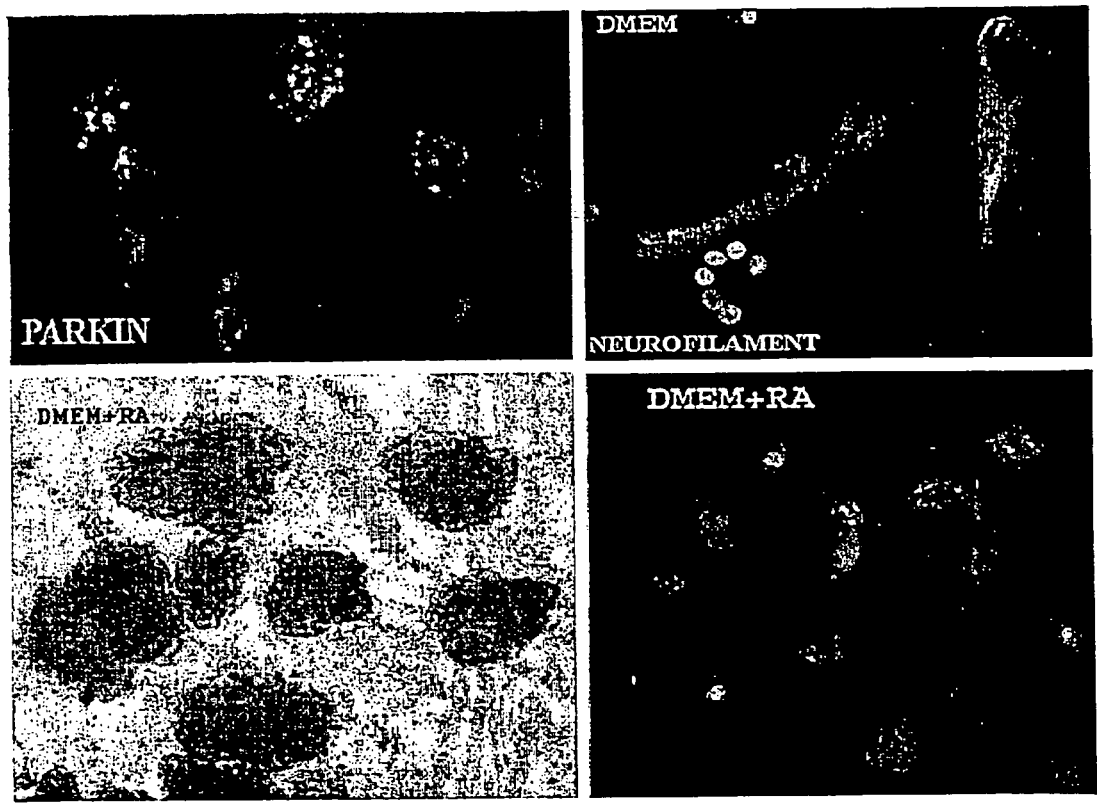

FIG. 14 shows neural positive cells. Lin⁻ cells grown for 7-14 days are positive for nestin mRNA by PCR FIG. 15 shows the immunocytochemistry of neural cells. Lin⁻ cells pre-grown in Fgft SCF and Flt3 ligand then placed into DME+ serum are positive for neuroffiament and Parkin. The addition of Retinoic acid(RA) results in first the formation of neurospheres and with further culturing, neurofilament positive cells. RA kills off the non-neural cells in the culture.

Figure 16:
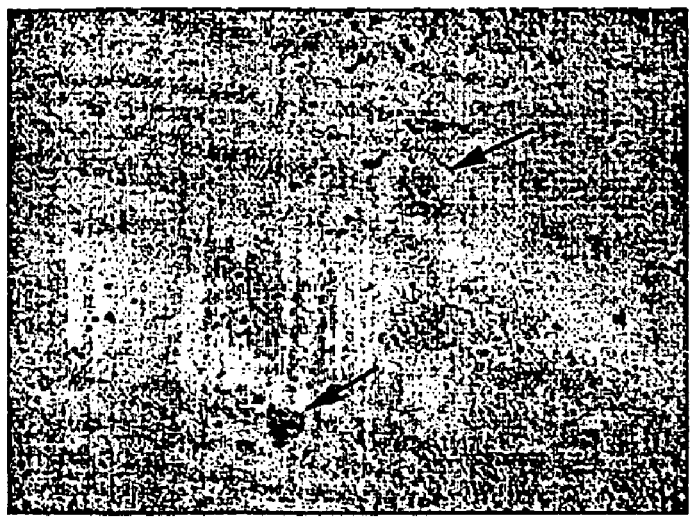

FIG. 16 shows adipocyte positive cells. Under the same conditions that result in osteoclast growth, adipocytes can be detected. Sudan IV stain was used to detect adipocyte cells in the cell cultures.

Figure 17:
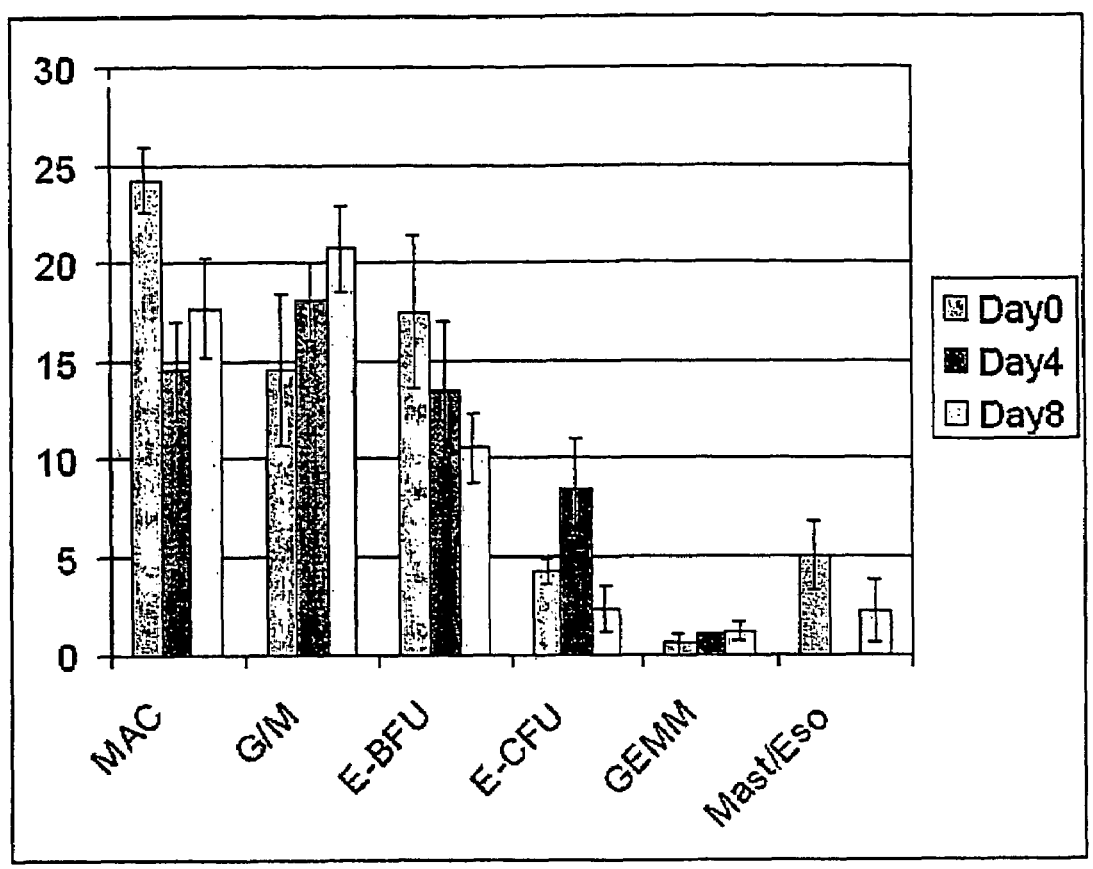

FIG. 17 Lin⁻ cells were grown in FGF, SCF, FLT3 ligand for 0, 4 or 8 days. Cell prolifetation of ~3x occurred over the 8 days. 500 cells/assay were used and colonies counted after 16 days. There is no significant difference between the three groups. This indicated that the expanded cells are equivalent to the untreated population.

DETAILED DESCRIPTION OF A PREFERRED EMBODIMENT

In accordance with the present invention there may be employed conventional molecular biology, microbiology, and recombinant DNA techniques within the skill of the art. Such techniques are explained fully in the literature. See for example, Sambrook, Fritsch, & Maniatis (2); DNA Cloning: A Practical Approach, Volumes I and II (D. N. Glover ed. 1985) (3); Oligonucleotide Synthesis (M. J. Gait ed. 1984) (4); Nucleic Acid Hybridization B. D. Hames & S. J. Higgins eds. (1985)(5); Transcription and Translation B. D. Hames & S. J. Higgins eds (1984) (6); Animal Cell Culture R. I. Freshney, ed. (1986) (7); Immnobilized Cells and enzymes IRL Press, (1986) (8); and B. Perbal, A Practical Guide to Molecular Cloning (1984) (9). The invention may also employ standard methods in immunology known in the art such as described in Stites et al.(10); and Mishell and Shigi (11).

For convenience, certain terms employed in the specification and claims are collected here.

"Patient" refers to an animal preferably a human, to whom treatment, including prophylactic treatment, with the cells, preparations, and compositions of the present invention, is provided. For treatment of those conditions or disease states that are specific for a specific animal such as a human patient, the term refers to that specific animal. A "donor" refers to an individual (animal including a human) who or which donates hematopoietic cells, in particular umbilical cord blood for use in a patient.

"Effective amount" refers to concentrations of components such as growth factors, cells, preparations, or compositions effective for producing an intended result including proliferation of hematopoietic stem and progenitor cells, or treating a disease or condition with cells, preparations, and compositions of the invention, or for effecting a transplantation of cells within a patient to be treated.

The terms "administering" or "administration" refers to the process by which cells, preparations, or compositions of the invention are delivered to a patient for treatment purposes: Cells, preparations, or compositions may be administered a number of ways including parenteral(e.g. intravenous and intraarterial as well as other appropriate parenteral routes), oral subcutaneous, inhalation, or transdermal. Cells, preparations, and compositions of the invention are administered in accordance with good medical practices taking into account the patient's clinical condition, the site and method of administration, dosage, patient age, sex, body weight, and other factors known to physicians.

"Transplanting", "transplantation", "grafting" and "graft" are used to describe the process by which cells, preparations, and compositions of the invention are delivered to the site within the patient where the cells are intended to exhibit a favorable effect, such as repairing damage to a patient's tissues, treating a disease, injury or trauma, or genetic damage or environmental insult to an organ or tissue caused by, for example an accident or other activity. Cells, preparations, and compositions may also be delivered in a remote area of the body by any mode of administration relying on cellular migration to the appropriate area in the body to effect transplantation.

"Essentially" refers to a population of cells or a method which is at least 20+%, 30+%, 40+%, 50+%, 60+%, 70+%, 80+%, 85+%, 90+%, or 95+% effective, more preferably at least 98+% effective, most preferably 99+% effective. Therefore, a method that enriches for a given cell population, enriches at least about 20+%, 30+%, 40+%, 50+%, 60+%, 70+%, 80%, 85%, 90%, or 95% of the targeted cell population, most preferably at least about 98% of the cell population, most preferably about 99% of the cell population. In certain embodiments the cells in an enriched hematopoietic cell population of the invention comprise essentially CD45⁺ HLA-ABC⁺ cells, or preferably CD45⁺HLA-ABC⁺Lin⁻ cells. In other embodiments, a cellular composition of the invention comprises essentially cells with the potential or increased potential to form non-hematopoietic cells.

"Isolated" or "purified" refers to altered "by the hand of man" from the natural state i.e. anything that occurs in nature is defined as isolated when it has been removed from its original environment, or both. In an aspect, a population or composition of cells is substantially free of cells and materials with which it may be associated in nature. By substantially free or substantially purified is meant at least 50% of the population are the target cells, preferably at least 70%, more preferably-at least 80%, and even more preferably at least 90% are free of other cells. Purity of a population or composition of cells can be assessed by appropriate methods that are well known in the art.

The "fibroblast growth factor receptor" or "FGF receptor" or "FGF-R" refers to proteins that bind to a family of related growth factor ligands, the fibroblast growth factor(FGF) family. The term includes the four FGF transmembrane protein tyrosine kinases, (12, 50), and variants thereof which may be cell bound or secreted forms. FGFR1 and FGFR2 bind acidic FGF/FGF1 and basic FGF/FGF2 with similar affinity (13). FGFRs bind FGF1 and FGF4 (hst/kfgf)with moderate to high affinity, while FGFR3 binds to only FGF1 and FGF4 (14, 15). The term also encompasses FGFR6, FGFR16, FGFR17, FGFR18, and FGFR19. See Moroni E et al (51) and Goldfarb M. (52) describing fibroblast growth factors and their receptors.

The "flt3 receptor" or "flt3" refers to proteins belonging to a family of structurally related tyrosine kinase receptors that contain five extracellular immunoglobulin (Ig)-like domains and an intracellular tyrosine kinase domain (Small et al., Proc. Natl. Acad. Sci. 91:459-463 (1994)). See Gilliland D G and Griffin J D. (53) for a review of FLT3.

The stem cell factor (SCF) receptor [synonyms: CD117 protein, SCF receptor or c-lit receptor (17)], is localized in the plasma membrane of blood stem cells and is encoded by the proto-onkogen c-kit (18). See Smith M A et al (54) for a review of stem cell factor.

"Gene therapy" refers to the transfer and stable insertion of new genetic information into cells for the therapeutic treatment of diseases or disorders. A foreign gene is transferred into a cell that proliferates to introduce the transferred gene throughout the cell population. Therefore, cells and compositions of the invention may be the target of gene transfer, since they will produce various lineages which will potentially express the foreign gene.

As used herein, "hematopoietic cells" refers to cells that are related to the production of blood cells, including cells of the lymphoid, myeloid and erythroid lineages. Exemplary hematopoietic cells include hematopoietic stem cells, primordial stem cells, early progenitor cells, $CD34^+$ cells, early lineage cells of the mesenchymal, myeloid, lymphoid and erythroid lineages, bone marrow cells, blood cells, umbilical cord blood cells, stromal cells, and other hematopoietic precursor cells that are known to those of ordinary skill in the art. The hematopoietic cells may be obtained from fresh blood, reconstituted cryopreserved blood, or fresh or reconstituted fractions thereof.

The hematopoietic cells (and the cells in the preparations and compositions of the invention) are preferably mammalian cells, more preferably, the cells are primate, pig, rabbit, dog, or rodent (e.g. rat or mouse) in origin Most preferably, the cells are human in origin. The hematopoietic cells may be obtained from a fetus, a child, an adolescent, or an adult The most desirable source of the hematopoietic cells is umbilical cord blood (UCB). "Umbilical cord blood" generally refers to blood obtained from a neonate or fetus. In a preferred embodiment, umbilical cord blood refers to blood obtained form the umbilical cord or placenta of newborns. Hematopoietic cells obtained from UCB offer several advantages including less invasive collection and less severe graft versus host (GVH) reaction (19). The use ofumbilical cord blood also eliminates the use of human embryos as a source of embryonic stem cells. Cord blood may be obtained by direct drainage from the cord and/or by needle aspiration from the delivered placenta at the root and at distended veins.

"Non-hematopoietic cells" include non-blood and non-lymph cells, including but not limited to muscle cells, neural cells, adipocytes, oseeoclasts, osteoblasts, endothelial cells, astrocytes,pancreatic cells (e.g. exocrine or endocrine pancreatic cells),retinal cells, renal cells, connective tissue cells, corneal cells, and hepatocytes.

"Cells with the potential or increased potential to form non-hematopoietic cells" refers to cells, preferably hematopoietic cells, that show at least one phenotypic characteristic of an early stage non-hematopoietic cell (e.g. stem, precursor, or progenitor non-hematopoietic cells), and preferably at least one phenotypic characteristic of an embryonic stem cell. Such phenotypic characteristic scan include expression of one or more proteins specific for early stage non-hematopoietic cells, or a physiological, morphological, immunological, or functional characteristic specific for an early stage non-hematopoietic cell or embryonic stem cell [e.g. Oct4, Stage Specific Embryonic Antigen-3 (SSEA3), and/or Stage Specific Embryonic Antigen-4 (SSEA4)].

Cells with potential or increase potential to form non-hematopoietic cells are produced by first obtaining hematopoietic cells and enriching the cells for hematopoietic stem cells and progenitor cells (sometimes referred to herein as "enriched hematopoictic cell preparation"). The term "stem cells" refers to undifferentiated cells that are capable of essentially unlimited propagation either in vitro, in vivo or ex vivo and capable of differentiation to other cell types. "Progenitor cells" are cells that are derived from stem cells by differentiation and are capable of further differentiation to more mature cell types. Negative and positive selection methods known in the ant can be used for enrichment of the hematopoietic cells. For example, cells can be sorted based on cell surface antigens using a fluorescence activated cell sorter, or magnetic beads which bind cells with certain cell surface antigens (e.g. CD45). Negative selection columns can be used to remove cells expressing lineage specific surface antigens.

In an aspect of the invention, an enriched hematopoietic cell preparation is provided wherein the cells in the preparation are characterized as follows:
  (a) $CD45^+MA-ABC^+$
  (b) $Lin^-$;
  (c) stem cell factor receptor+
  (d) FLT3 ligand receptor+;
  (e) FGF receptor+;
  (f) $CD34^+$;
  (g) $CD38^+$; and
  (h) $CD33^+$.

In an embodiment, an enriched hematopoietic cell preparation is provided comprising cells characterized by (a) and (b); or (a), (c), (d), and (e), and optionally (b), (f), (a), and/or (h).

An enriched hematopoietic cell preparation may comprise cells that are at least 70%, 80%, 90%, 95%, 98%, or 99% $CD45^+HLA-ABC^+Lin^-$ cells, 70%, 80%, 90%, 95%, 98%, or 99% stem cell factor receptor+,, 70%, 80%, 90%, 95%, 98%, or 99% Flt3ligand receptor+,, 70%, 80%, 90%, 95%, 98%, or 99% FGF receptor+, and it may optionally comprise at least 50-80% $CD34^+$ cells, at least 50-80% $CD38^+$ cells, and/or at least 50% $CD33^+$ cells.

In an embodiment, an enriched cell population of the invention is provided comprising the following:
  (a) at least 50% $CD34^+$ cells, preferably 60 to 95%, more preferably 65% to 90%, or most preferably about 65% $CD34^+$ cells;

(b) about 5 to 50%, preferably 5 to 25%, more preferably 5 to 15%, most preferably about 10% of the cells in (a) are CD33⁻ and CD38⁻;

(c) at least 50% CD34⁻; preferably 15 to 40%, more preferably 15% to 40%, or most preferably about 35% CD34⁺ cells;

(d) about 5 to 50%, preferably 5 to 25%, more preferably 5 to 15%, most preferably about 10% of the cells in (c) are CD33⁺ or CD38⁺ and the remaining cells are negative for all hematopoietic cell surface antigens;

(e) about 5 to 50%, preferably 5 to 25%, more preferably 5 to 20%, most preferably about 5% are CD33⁺; and (f) about 20 to 60%, preferably 25 to 55%, more preferably 35 to 45%, most preferably 40% are CD38⁺.

The enriched hematopoietic cell preparation can be cultured under proliferation conditions to produce cells that have potential or increased potential to form different types of non-hematopoietic cells and tissues. The enriched preparation of hematopoietic stem cells and progenitor cells may be cultured in vitro or in vivo, preferably in vitro. The proliferation conditions are those conditions that give rise to cells that have the potential or increased potential to form non-hematopoietic cells and tissues.

The proliferation conditions involve culturing the cells in the presence of one or more positive growth factors for a sufficient time to enable the cells to complete sufficient cell cycles to develop tissue potential or increased tissue potential. Positive growth factors are growth factors that promote and maintain cell proliferation. Growth factors such as TGFβ and TNFα that promote differentiation are not suitable for use in the proliferation conditions of the method of the invention.

The positive growth factors maybe human in origin, or may be derived from other mammalian species when active on human cells. The following are representative examples of positive growth factors which may be employed in the present invention: all members of the fibroblast growth factor (FGF) family including FGF-4 and FGF-2, epidermal growth factor (EGF), stem cell factor (SCF), thrombopoietin (TPO), FLT-3 ligand, interleukin-3 (Il-3), interleukin-6 (IL-6), neural growth factor (NGF), VEGF, Granulocyte-Macrophage Growth Factor (GM-CSF), HGF, Hox family, and Notch In a prefered embodiment of the invention the cells are cultured in the absence of EGF.

Preferably the positive growth factors or combination of growth factors used in the present invention are fibroblast growth factor (FGF) (e.g. FGF-4 and FGF-2), IL-3, stem cell factor (SCF), FLT3 ligand, thrombopoietin (TPO), granulocyte macrophage-colony stimulating factor (GM-CSF), and neural growth factor (NGF). In embodiments of the invention, FGF (e.g. FGF-4 or FGF-2) is used with SCF and FLT3 ligand; FGF is used with TPO; or TPO is used with SCF and FLT3 ligand.

In an aspect of the invention the proliferation conditions involve using FGF-4 or FGF-2, SCF and FLT3 ligand to prepare cellular compositions to produce non-hematopoietic cells such as osteoclasts, osteoblasts, muscle cells, endothelial cells, hepatocytes, astrocytes, neural cells, and/or adipocytes. In another aspect the proliferation conditions involve using TPO, SCF and FLT-3 ligand to prepare cellular compositions to produce non-hematopoietic cells such as endothelial cells. In another aspect the proliferation conditions involve using NGF, SCF, and FLT-3 to prepare cellular compositions to produce non-hematopoietic cells such as endothelial cells or others.

The growth factors may be used in combination with equal molar or greater amounts of a glycosaminoglycan such as heparin sulfate.

Growth factors may be commercially available or can be produced by recombinant DNA techniques and purified to various degrees. For example, growth factors are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). Some growth factors may be purified from culture media of cell lines by standard biochemical techniques. Thus, it is intended that molecules having similar biological activity as wild-type or purified growth factors (e.g., recombinantly produced or mutants thereof) are intended to be used within the spirit and scope of the invention.

An effective amount of a positive growth factor is used in the culture medium. Generally, the concentration of a positive growth factor in the culture medium is between 10 and 150 ng/ml, preferably 25 to 100 ng/ml. The growth factors are typically applied at sufficient intervals to maintain high proliferation levels and maintenance of a stem cell phenotype. In an embodiment, the growth factors are applied about 2-4 times per week, preferably 2-3 times per week.

The culture medium may comprise conditioned medium, non-conditioned medium, or embryonic stem cell medium. Examples of suitable conditioned medium include IMDM, DMEM, or αMEM, conditioned with embryonic fibroblast cells (e.g. human embryonic fibroblast cells or mouse embryonic fibroblast cells), or equivalent medium. Examples of suitable non-conditioned medium include Iscove's Modified Delbecco's Medium (IMDM), DMEM or αMEM or equivalent medium. The culture medium may comprise serum (e.g. bovine serum, fetal bovine serum, calf bovine serum, horse serum, human serum, or an artificial serum substitute [e.g. 1% bovine serum albumin, 10 μg/ml bovine pancreatic insulin, 200 μg/ml human transferring, $10^{-4}$M β-mercaptoethanol, 2 mM L-glutamine and 40 μg/ml LDL (Low Density Lipoproteins)], or it may be serum free.

In an embodiment, the culture medium is serum free to provide cells with the potential or increased potential to form non-hematopoietic cells that are free of serum proteins or biomolecules that may bind to the surface of the cells. Cells cultured in such conditions may provide non-hematopoietic cells that have potential exposed novel antigenic sites. Such cells may be useful as immunogens. Thus, the invention provides a cellular composition or mitotic or differentiated cells therefrom that are isolated and maintained in serum-free media.

The proliferation conditions entail culturing the enriched cell preparation for a sufficient period of time so that cells in the preparation develop potential or an increased potential to form non-hematopoietic cells and tissues. The cells are generally maintained so that the cells complete about 1-100 cell cycles, preferably 5-75 cell cycles; more preferably 2-50,2-40 or 2-20, most preferably at least about 2-10 or 4-5 cell cycles. This will typically correspond to about 4 to 40 days in culture, preferably about 2-20 days in culture, more preferably at least or about 2-15 days or 4-10 days in culture, and most preferably at least about 4-8 days in culture.

The frequency of feeding the enriched hematopoietic cell preparation is selected to promote the survival and growth of cells with the potential or increased potential to form non-hematopoietic cells. In an embodiment the cells are fed once or twice a week. The cells may be fed by replacing the entirety of the culture media with new media.

The cells in culture may be selected for hematopoietic stem and progenitor cells (e.g. CD45⁺HLA-ABC⁺ cells) at a frequency to promote the survival and growth of cells with the potential or increased potential to form non-hematopoietic cells. In a preferred embodiment of a method of the invention, cells that are enriched for hematopoietic stem and progenitor cells (e.g. CD45+ HLA-ABC+ cells) are reselected at intervals, preferably weekly, through positive or negative selection techniques known in the art and described herein.

The methods of the invention may be conducted on a large-scale, for example a cellular composition of the invention may be isolated and/or expanded in a bioreactors.

The method of the present invention leads to a newly created cellular composition comprising a population of cells with the potential or increased potential to form hematopoietic and non-hematopoietic cells in vitro and in vivo. The cells may have an altered differentiation program enabling the cells to form non-hematopoietic cells. The cells may have the potential to differentiate into cells that exhibit morphological, physiological, functional and/or immunological features of non-hematopoietic cells. The cells may be further characterized by embryonic or early non-hematopoietic tissue markers (e.g. the early muscle marker Desmin).

In an aspect of the invention, an isolated and purified cellular composition is provided comprising or comprising essentially cells characterized by one or more of the following:
  (a) CD45+HLA-ABC+
  (b) Capable of differentiating into hematopoietic cells or hematopoietic progenitor cells;
  (c) Capable of differentiating into one or more, two or more, three or more, four or more, five or more, or six or more, different non-hematopoietic cell types, including mesenchymal stem or progenitor cells, neural stem or progenitor cells, or endothelial stem or progenitor cells; in particular, for example, endothelial cells, osteoclasts, osteoblasts, adipocytes, muscle cells, astocytes, and neural cells;
  (d) round shape and non-adherent growth requirements;
  (e) stem cell factor receptor (KIT)+
  (f) FLT3 ligand receptor+;
  (g) FGF receptor+;
  (h) express embryonic stem cell proteins such as Oct4, Stage Specific Embryonic Antigen-3 (SSEA3), and/or Stage Specific Embryonic Antigen-4 (SSEA4);
  (i) HoxB4+;
  (j) Flk-1+;
  (k) CD34$^\pm$;
  (l) non-tumorigenic, i.e. the cells do not give rise to neoplasm or tumor or are free from neoplasia and cancer,
  (m) CD38$^\pm$; and
  (n) derived from umbilical cord blood.

A cellular composition may comprise cells with the characteristics (a) and (c); (a), (b), and (c); (a), (b), (c) and (d); (a), (b), (c), (d) and (e); (a), (b), (c), (d), (e), (f), and (g); (a) through (e) inclusive; (a) through (f) inclusive; (a) through (g) inclusive; (a) through (h) inclusive; (a) through (i) inclusive; (a) through (j) inclusive; (a) through (j) inclusive, and (k); (a) through (j) inclusive and (l) and (k); (a) through (j) inclusive, and (l) and (m); (a) through (j) inclusive, and (l), (m), and (n); or (a) through (i) inclusive and (k); (a) through (i) inclusive and (k) and (l); (a) through (i) inclusive and (k), (l), and (m); (a) through (i) inclusive and (k), (l), (m) and (n). In a preferred embodiment, an enriched cell preparation is provided comprising cells with the characteristics (a), (b), (c) (d) and (e).

Cellular compositions of the invention may also be prepared using positive or negative selection techniques based on one or more of the characteristics of the cells of the composition as described herein.

Cells with the potential or increased potential to form non-hematopoietic cells may be induced to differentiate into cells and tissues of non-hematopoietic lineages in vitro or in viva. These cells may also provide hematopoietic cells (e.g. stem and/or progenitor cells), preferably an expanded hematopoietic cell preparation.

The cells with potential or increased potential to form non-hematopoietic cells may be induced to differentiate into cells of non-hematopoietic cell lineages, preferably cells that exhibit morphological, physiological functional, and/or immunological features of non-hematopoietic cells. Cells from a differentiated cell preparation may be characterized by expression of genetic markers of non-hematopoietic cell lineages (e.g. markers for muscle, neural, adipodte, osteoclast, osteoblast, endothelial, astrocytes, pancratic cells, retinal cells, renal cells, connective tissue cells, and hepatocytes), or physiological, immunological or functional characteristics of cells of non-hematopoietic lineages. For example, non-hematopoietic cells can be screened for expression of tissue specific markers such as Myo-D (muscle), FLK-1 (endothelial), glial fibrillary acidic protein (astrocytes), glucagon (alpha-α cells), insulin (islet-β cells), somatostatin (islet-δ), pancreatic polypeptide (islet-PP cells), cytokeratins (CK), mucin MUC1, carbonic anyhydrase II, and carbohydrate antigen 19.1 (ductal cells), and NESTIN (neural).

In an aspect of the invention, the invention provides a method for producing an isolated and purified cell preparation comprising muscle cells, neural cells (neurons, astrocytes, type I and type II, and oligodendrocytes), adipocytes, osteoclasts, osteoblasts, endothelial cells, pancreatic cells (acinar, ductal, islet-α, islet-β, islet-δ, and islet-PP), kidney cells, retinal cells, corneal cells, connective tissue cells, or hepatocytes, using a cellular composition or method of the invention.

Differentiated cells can be used to prepare a cDNA library relatively uncontaminated with cDNA preferentially expressed in cells from other lineages, and they can be used to prepare antibodies that are specific for particular markers of non-hematopoietic cells.

In an embodiment, the cells in a cellular composition of the invention may be cultured in osteoclast differentiation medium (e.g. serum containing medium with GM-CSF) to differentiate the cells into functional osteoclasts. Osteoclasts may be identified by the ability of the cells to resorb calcium citrate substrate. The osteoclasts may be converted into osteoblasts by culturing in osteoblast specific differentiation medium. Osteoblasts may also be produced by culturing cells or a cellular composition of the invention on osteoblast differentiation medium (e.g. αMEM with dexamethasone, glycerolphosphate, ascorbic acid, and serum). Osteoblasts may be identified by expression of tissue specific markers such as CBFα.

Functional neural cells may be obtained by culturing cells of a cellular composition of the invention with a differentiation factor that induces formation of neural cells such as neural growth factor. Neural cells may be obtained by growing cells of a cellular composition of the invention on media that induces differentiation of the cells to neural cells (e.g. DMEM medium with serum and retinoic acid). Neural cells may be identified based on expression of neural specific markers such as neurofilament, NESTIN, and Parkin.

Muscle cells may be produced by culturing cells of a cellular composition of the invention with a differentiation factor that induces formation of muscle cells. The cells of a cellular composition of the invention may be cultured in specialized muscle specific cell culture media that may comprise a differentiation factor that induces differentiation of the cells to form muscle cells. Muscle cells may be identified by expression of mature muscle cell markers such as Myo-D and muscle specific actin.

Endothelial cells may be produced by culturing cell of a cellular composition of the invention with a differentiation factor that induces formation of endothelial cells. The cells of a cellular composition of the invention may be cultured in specialized endothelial cell cultures that may comprise a differentiation factor that induces differentiation of the cells to form endothelial cells. Endothelial cells may be identified based on expression of Flk-1 and/or CD31.

Hepatocytes may be produced by culturing cells of a cellular composition of the invention with a differentiation factor that induces formation of hepatocytes (e.g. n-butyrate). The cells of a cellular composition of the invention may be cultured in specialized cell cultures that may comprise a differentiation factor that induces differentiation of the cells to form hepatocytes. Hepatocytes may be identified based on expression of CYP1A2, alpha-fetoprotein, albumin, CK 19, and/or ICAM-I.

Astrocytes may be produced by culturing cells of a cellular composition of the invention with a differentiation factor that induces formation of astrocytes (e.g. G-5 astrocyte growth supplement). The cells of a cellular composition of the invention may be cultured in specialized cell cultures that may comprise a differentiation factor that induces differentiation of the cells to form astrocytes. Astrocytes may be identified based on expression of glial fibrillary acidic protein (GFAP).

A dipocytes may be produced by culturing cells of a cellular composition of the invention with a differentiation factor that induces formation of adipocytes. The cells of a cellular composition of the invention may be cultured in specialized cell cultures that may comprise a differentiation factor that induces differentiation of the cells to form adipocytes. Adipocytes may be identified based on positive staining with SudanIV or oil-o-red.

Similarly, renal cells, retinal cells, corneal cells, and connective tissue cells may be produced by culturing cells of a cellular composition of the invention with a differentiation factor that induces formation of the cells, or they may be cultured in specialized cell cultures that induce differentiation to form the cells. The cells may be identified based on expression of cell specific markers.

After differentiation of the cells into selected non-hematopoietic cells as described herein, the cells may be separated to obtain a population of cells largely consisting of the non-hematopoietic cells. This may be accomplished by positive selection of non-hematopoietic cells using antibodies to identify tissue specific cell surface markers or negative selection using hematopoietic cell specific markers.

Expansion of hematopoietic stem cells and progenitor cells in accordance with the invention can be carried out under proliferation conditions as described herein. In general, the same culturing conditions that are used for culturing cells to produce cells with potential or increased potential to form non-hematopoietic cells may be employed. An exemplary protocol for expanding hematopoietic stem cells and progenitor cells is provided in the Example.

Modification of Cells

A cell preparation or cellular composition of the invention may be derived from or comprised of cells that have been genetically modified (transduced or transfected) either in nature or by genetic engineering techniques in vivo or in vitro.

Cells in cell preparations and compositions of the invention can be modified by introducing mutations into genes in the cells (or the cells from which they are obtained) or by introducing transgenes into the cells. Insertion or deletion mutations may be introduced in a cell using standard techniques. A transgenes may be introduced into cells via conventional techniques such as calcium phosphate or calcium chloride co-precipitation, DEAE-dextran-mediated transfection, lipofection, electroporation, or microinjection. Suitable methods for transforming and transfecting cells can be found in Sambrook et al (2), and other laboratory textbooks. By way of example, a transgene may be introduced into cells using an appropriate expression vector including but not limited to cosmids, plasmids, or modified viruses (e.g. replication defective revruees, adenoviruses and adeno-associated viruses). Transfection is easily and efficiently obtained using standard methods including culturing the cells on a monolayer of virus-producing cells (20, 21).

A gene encoding a selectable marker may be integrated into cells of a cell preparation or composition of the invention. For example, a gene which encodes a protein such as $\beta$-galactosidase, chloramphenicol acetyltransferase, firefly luciferase, or a fluorescent protein marker may be integrated into the cells. Examples of fluorescent protein markers are the Green Fluorescent Protein (GFP) from the jellyfish *A. victoria*, or a variant thereof that retains its fluorescent properties when expressed invertebrate cells. (For example, the GFP variants described in references 22-24; and EGFP commercially available from Clontech Palo Alto, Calif.).

Another aspect of the present invention relates to genetically engineering the cells in the cell preparations and compositions of the invention in such a manner that they or cells derived therefrom produce, in vitro or in vivo, polypeptides, hormones and proteins not normally produced in the cells in biologically significant amounts, or produced in small amounts but in situations in which regulatory expression would lead to a therapeutic benefit. For example, the cells could be engineered with a gene that expresses a molecule that specifically inhibits bone resorption, but does not otherwise interfere with osteoclasts binding to bone, or the cells could be engineered with a gene that expresses insulin at levels compatible with normal injected doses. Alternatively the cells could be modified such that a protein normally expressed will be expressed at much lower levels. These products would then be secreted into the surrounding media or purified from the cells. The cells formed in this way can serve as continuous short term or long term production systems of the expressed substance.

Thus, in accordance with this aspect of the invention, cells with the potential or increased potential to form non-hematopoietic cells can be modified with genetic material of interest. The modified cells can be cultured in vitro under suitable conditions so that they differentiate into specific non-hematopoietic cells. The non-hematopoietic cells are able to express the product of the gene expression or secrete the expression product. These modified cells can be administered to a target tissue where the expressed product will have a beneficial effect.

In a further embodiment, the transduced cells with the potential or increased potential to form non-hematopoietic cells can be induced in vivo to differentiate into non-hematopoietic cells that will express the gene product. For example, the transduced cells may be administered to induce production of non-hematopoietic cells having the transduced gene. The cells may be administered in admixture with each other or separately and maybe delivered to a targeted area. The cells can be introduced intravenously and home to the targeted area. Alternatively, the cells may be used alone and caused to differentiate in vivo.

Thus, genes can be introduced into cells which are then injected into a recipient where the expression of the gene will have a therapeutic effect For example, osteoclasts may be genetically engineered to have reduced activity in viva Appropriate genes would include those that play a role in the regulation of osteoporosis, in areas such as serum calcium responsiveness, estrogen secretion and bone resorption. An insulin gene may be introduced into blood stem cells to provide a constant therapeutic dose of insulin in the bone marrow and peripheral blood.

The technology may be used to produce additional copies of essential genes to allow augmented expression by non-hematopoietic cells of certain gene products in viva These genes can be, for example, hormones, matrix proteins, cell membrane proteins, cytokines, adhesion molecules, or "rebuilding" proteins important in tissue repair.

Applications

The cell preparations and compositions of the invention can be used in a variety of methods (e.g. transplantation) and they have numerous uses in the field of medicine. They may be used for the replacement of body tissues, organs, components or structures which are missing or damaged due to trauma, age, metabolic or toxic injury, disease, idiopathic loss, or any other cause.

Transplantation or grafting, as used herein, can include the steps of isolating a cell preparation according to the invention and transferring cells in the preparation into a mammal or a patient. Transplantation can involve transferring the cells into a mammal or a patient by injection of a cell suspension into the mammal or patient, surgical implantation of a cell mass into a tissue or organ of the mammal or patient, or perfusion of a tissue or organ with a cell suspension. The route of transferring the cells may be determined by the requirement for the cells to reside in a particular tissue or organ and by the ability of the cells to find and be retained by the desired target tissue or organ. Where the transplanted cells are to reside in a particular location, they can be surgically placed into a tissue or organ or simply injected into the bloodstream if the cells have the capability to migrate to the desired target organ.

The invention may be used for autografting (cells from an individual are used in the same individual), autografting cells (cells from one individual are used in another individual) and xenografting (transplantation from one species to another). Thus, the cells, cell preparations and cellular compositions of the invention may be used in autologous or allogenic transplantation procedures to improve a non-hematopoietic cell or hematopoietic cell deficit or to repair tissue.

In an aspect of the invention, the newly created cellular compositions comprising cells with potential or increased potential to form non-hematopoietic cells, or non-hematopoietic cells differentiated therefrom, can be used in both cell therapies and gene therapies aimed at alleviating disorders and diseases involving the non-hematopoietic cells. The invention obviates the need for human tissue to be used in various medical and research applications.

The cell therapy approach involves the use of transplantation of the newly created cellular compositions comprising cells with the potential or increased potential to form non-hematopoietic cells, or non-hematopoietic cells differentiated therefrom, as a treatment for injuries and diseases. The steps in this application include: (a) producing a cellular composition comprising cells with the potential or increased potential to form non-hematopoietic cells, or non-hematopoietic cells differentiated therefrom, as described herein; and (b) allowing the cells to form functional connections either before or after a step involving transplantation of the cells.

The gene therapy approach also involves cellular compositions comprising cells with the potential or increased potential to form non-hematopoietic cells, however, following the culturing step in proliferation conditions, the newly created cells are transfected with an appropriate vector containing a cDNA for a desired protein, followed by a step where the modified cells are transplanted.

In either a cell or gene therapy approach, therefore, cells with potential or increased potential to form non-hematopoietic cells and hematopoietic cells in cellular compositions of the present invention, or cells or tissues differentiated from the cells can be transplanted in, or grafted to, a patient in need. Thus, the cells with potential to form non-hematopoietic cells or differentiated cells therefrom can be used to replace non-hematopoietic cells in a patient in a cell therapy approach, useful in the treatment of tissue injury, and diseases. These cells can be also used as vehicles for the delivery of specific gene products to a patient. One example of how these newly created cells or cell differentiated therefrom can be used in a gene therapy method is in treating the effects of Parkinson's disease. For example, tyrosine hydrolase, a key enzyme in dopamine synthesis, may be delivered to a patient via the transplantation of a cell preparation of the invention comprising cells that are capable of differentiating into neuronal cells, or transplantation of neuronal cells differentiated from the cells, which have been transfected with a vector suitable for the expression of tyrosine hydrolase.

The invention also provides a method of treating a patient with a condition involving a non-hematopoietic cell comprising transferring a cellular composition comprising cells with the potential or increased potential to form non-hematopoietic cells into the patient, wherein the cell differentiates into the non-hematopoietic cells.

The invention provides a method for obtaining non-hematopoietic cells for autologous transplantation from a patient's own hematopoietic cells comprising (a) obtaining a sample comprising hematopoietic cells from the patient, preferably from fresh or cryopreserved umbilical cord blood; (b) separating out an enriched cell preparation comprising hematopoietic stem cells and hematopoietic progenitor cells, preferably CD45$^+$HLA-ABC$^+$ cells; and (b) culturing the cells under proliferation conditions to produce a cellular composition comprising cells with the potential or increased potential to form non-hematopoietic cells. The cellular composition obtained from (b) can be cultured with a differentiating factor, or cells of the composition can be transferred to the patient.

The invention also contemplates a pharmaceutical composition comprising cells, a cell preparation, or cellular composition of the invention, and a pharmaceutically acceptable carrier, excipient, or diluent. The pharmaceutical compositions herein can be prepared by per se known methods for the preparation of pharmaceutically acceptable compositions which can be administered to subjects, such that an effective amount of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the cells, cell preparations, or cellular compositions in association with one or more pharmaceutically acceptable vehicles or diluents, and contained in buffered solutions with a suitable pH and iso-osmotic with the physiological fluids.

Still another aspect of the invention is a kit for producing cellular compositions of the invention comprising cells that have potential or increased potential to form cells capable of differentiating into cells of multiple tissue types both in vitro and in vivo. The kit includes the reagents for a method of the present invention for producing a cellular composition. This kit preferably would include at least one positive growth factor, and instructions for use.

In an aspect, cells, cell preparations, and cellular compositions disclosed herein can be used for toxicity testing for drug development testing. Toxicity testing may be conducted by culturing cells, cell preparations, and cellular compositions or cells differentiated therefrom in a suitable medium and introducing a substance, such as a pharmaceutical or chemical, to the culture. The cells or differentiated cells are examined to determine if the substance has had an adverse effect on the culture. Drug development testing may be done by developing derivative cell lines which may be used to test the efficacy of new drugs. Affinity assays for new drugs may also be developed from the cells, differentiated cells, or cell lines.

Using a method of the invention it is possible to identify drugs that are potentially toxic to non-hematopoietic or hematopoietic cells.

The cellular compositions of the invention may be used to screen for potential therapeutics that modulate development or activity of cells with the potential to form non-hematopoietic cells or cells differentiated there from. In particular, the cells of a cellular composition of the invention may be subjected to a test substance, and the effect of the test substance may be compared to a control (e.g. in the absence of the substance) to determine if the test substance modulates development or activity of the cells with the potential to form non-hematopoietic cells or cells differentiated therefrom.

In an aspect of the invention a method is provided for using cells with the potential or increased potential to form non-hematopoietic cells or cells differentiated therefrom to assay the activity of a test substance comprising the steps of a) culturing cells in an enriched hematopoietic cell preparation comprising hematopoietic stem cells and progenitor cells under proliferation conditions to obtain a cellular composition comprising cells which have potential or increased potential to form non-hematopoietic cells;

b) optionally culturing the cells which have potential or increased potential to form non-hematopoietic cells under differentiation conditions in vitro;

c) exposing the cultured cells in step (a) or (b) to a test substance; and d) detecting the presence or absence of an effect of the test substance on the survival of the cells or on a morphological functional, or physiological characteristic and/or molecular biological property of the cells, whereby an effect altering cell survival, a morphological, functional, or physiological characteristic and/or a molecular biological property of the cells indicates the activity of the test substance.

In another aspect a method is provide for using cells with the potential or increased potential to form non-hematopoietic cells or cells differentiated therefrom to screen a potential new drug to treat a disorder involving the non-hematopoietic cells comprising the steps of:

(a) obtaining hematopoietic cells from a sample from a patient with a disorder involving non-hematopoietic cells;

(b) preparing from the hematopoietic cells an enriched hematopoietic cell preparation comprising hematopoietic stem cells and progenitor cells;

(c) culturing the enriched hematopoietic cell preparation under proliferation conditions to obtain cells with potential or increased potential to form the non-hematopoietic cells;

(d) optionally culturing the cells with potential or increased potential to form the non-hematopoietic cells under differentiation conditions in vitro;

(e) exposing the cultured cells in (c) or (d) to a potential new drug; and (f) detecting the presence or absence of an effect of the potential new drug on the survival of the cells or on a morphological, functional, or physiological characteristic and/or molecular biological property of said cells, whereby an effect altering cell survival a morphological, functional, or physiological characteristic and/or a molecular biological property of the cells indicates the activity of the potential new drug.

The invention also relates to the use of cells, cell preparations, and cellular compositions in drug discovery. The invention provides methods for drug development using the cells, cell preparations, and cellular compositions of the invention. Cells, cell preparations, and cellular compositions of the invention may comprise cells that secrete novel or known biological molecules or components. In particular, culturing in the absence of serum may provide cells that. have minimal interference from serum molecules and thus, may be more physiologically and topologically-accurate. Therefore, proteins secreted by cells described herein maybe used as targets for drug development. In one embodiment, drugs can be made to target specific proteins on cells that have the potential or increased potential to form non-hematopoietic cells. Binding of the drug may promote differentiation of cells into specific non-hematopoietic cells. In another embodiment, drugs specific for regulatory proteins of non-hematopoietic cells may be used to arrest growth of a particular type of cell. Any of the proteins can be used as targets to develop antibody, protein, antisense, aptamer, ribozymes, or small molecule drugs.

Agents, test substances, or drugs identified in accordance with a method of the invention or used in a method of the invention include but are not limited to proteins, peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies[e.g. polyclonal, monoclonal, humanized, anti-idiotypic, chimeric, single chain antibodies, fragments, (e.g. Fab, F(ab)2, and Fab expression library fragments, and epitope-binding fragments thereof)], nucleic acids, ribozymes, carbohydrates, and small organic or inorganic molecules. An agent, substance or drug may be an endogenous physiological compound or it may be a natural or synthetic compound.

The cells, cell preparations, and cellular compositions disclosed herein can be used in various bioassays. In an embodiment, the cells are used to determine which biological factors are required for proliferation or differentiation. By using cells that have the potential or increased potential to form non-hematopoietic cells and hematopoietic cells in a stepwise fashion in combination with different biological compounds (such as hormones, specific growth factors, etc.), one or more specific biological compounds can be found to induce differentiation to non-hematopoietic cells. Other uses in a bioassay for the cells are differential display (i.e. mRNA differential display) and protein-protein interactions using secreted proteins from the cells. Protein-protein interactions can be determined with techniques such as a yeast two-hybrid system.

Proteins from cells, cell preparations and cellular compositions of the invention can be used to identify other unknown proteins or other cell types that interact with the cells. These unknown proteins may be one or more of the following: growth factors, hormones, enzymes, transcription factors, translational factors, and tumor suppressors. Bioassays involving cells, cell preparations, and cellular compositions of the invention, and the protein-protein interactions these cells form and the effects of protein-protein or cell-cell contact may be used to determine how surrounding tissue contributes to proliferation or differentiation of non-hematopoietic and hematopoietic cells.

In an aspect of the invention cells with potential or increased potential for forming non-hematopoietic cells obtained after culturing a preparation from cord blood stem cells maybe used to repair cell or tissue injury. They may also be used in the treatment of genetic defects that result in nonfunctional cells. The cord blood stem cells grown in proliferation medium may be transplanted directly to the site of defective cells in order to rescue the defect or delivered via the blood stream by injecting the cells into the vein. In addition, gene therapy vectors may be integrated into the cord blood stem cells followed by engraftment of these engineered cells to their target tissues. The introduction of gene therapy vectors requires cell proliferation. The successful long term engraftment of the cells to the target tissue requires they maintain a stem cell characteristic. High proliferation rates of cord stem cells has been achieved without differentiation, which should lead to successful gene therapy.

In an embodiment, hepatocytes obtained from differentiating cells of a cellular composition of the invention, preferably derived from umbilical cord blood, or precursor cells thereof, may be used to restore a degree of liver function to a subject needing such therapy, perhaps due to an acute, chronic, or inherited impairment of liver function. Thus, they may be used to treat liver disease or repair liver damage. In particular, hepatocytes obtained in accordance with the present invention may be used to treat a number of degenerative liver diseases. Non-functional liver cells where there is no apparent physical damage may be treated through partial hepatectomy, followed by therapy using hepatocytes obtained using the present invention. The hepatocytes may be encapsulated, or part of a bioartificial liver device.

In another embodiment, endothelial cells obtained from differentiating cells of a cellular composition of the invention, preferably derived from umbilical cord blood, or precursor cells thereof may be used for vascular repair and they can be used in cardiopulmonary bypass surgery. Endothelial cells may be transfected with genes which produce angiogenic factors and used in gene therapy to stimulate angiogenesis in patients with vascular or cardiac insufficiency.

In still another embodiment, muscle cells obtained from differentiating cells of a cellular composition of the invention, preferably derived from umbilical cord blood, or precursor cells thereof, may be employed to repair muscle, in particular striated or cardiac muscle. Thus, the present invention may be used to treat degenerative muscle disease. The cells may be used in treating muscular dystrophy, cardiomyopathy, congestive heart failure; and myocardial infarction, for example. Genetic muscle disorders and cardiac muscle disorders may be treated using precursor muscle cells obtained using methods of the present invention. If muscle loss is due to the lack of neuronal connection (neuro-muscular disease), both the neural and muscle tissues can be replaced using cells obtained using the present invention.

In a further embodiment, neural cells obtained from differentiating cells of a cellular composition of the invention, preferably derived from umbilical cord blood, or precursor cells thereof maybe used for treating neurodegenerative disorders, a brain or spinal cord injury, or neurological deficit Neurodegenerative disorders which can be treated include for example, Parkinson's disease, Huntington's disease, multiple sclerosis, Alzheimer's disease, Tay Sach's disease, lysosomal storage disease, brain and/or spinal cord injury due to ischemia, stroke, head injury, cerebral palsy, spinal cord and brain damage/injury, depression, epilepsy, schizophrenia, and ataxia and alcoholism.

Neural cells generated in accordance with a method of the invention may be transfected with a vector that can express growth factors, growth factor receptors, and peptide neurotransmitters, or express enzymes involved in the synthesis of neurotransmitters. These transfected cells may be transplanted into regions of neurodegeneration.

In a still further embodiment, bone or cartilage cells obtained from differentiating cells of a cellular composition of the invention, preferably derived from umbilical cord blood, or precursor cells thereof, may be used to repair bone, and in reconstructive surgery or degenerative diseases. Artificial substrates or matrices can be used in combination with the cells to reconstitute tissues, implanted into the joints of patients to replace or repair damaged or deficient cartilage. The cartilage cells may be useful in the treatment of diseases of the joint, for example, osteoarthritis, inflammatory arthropathies, septic arthritis, and crystalline arthropathies, and they can be used to enhance healing of bone fractures when inserted into the site of a fracture. The cells can also be used in the study and treatment of chondrodysplasias, and to test angiogenic factors.

Retinal cells or precursor cells thereof generated in accordance with a method of the invention may be used to restore vision lost when retinal cells are damaged, and they can be used as in vivo targets for stimulation by growth factors in order to produce healthy tissue. In particular the cells may be used to treat conditions such as glaucoma, macular degeneration, diabetic retinopathies, inherited retinal degeneration such as retinitis pigmentosa, retinal detachment or injury and retinopathies (whether inherited, induced by surgery, trauma, a toxic compound or agent, or, photically; in particular, diabetic retinopathy).

Connective tissue cells or precursor cells thereof, generated in accordance with a method of the invention may be seeded onto matrices or substrates and used to repair or regenerate damaged tissue (e.g. tendons). Thus the invention contemplates a method for de novo formation of connective tissue in vivo by introducing connective tissue cells produced by a method of the invention into a site for de novo connective tissue formation in a patient in need thereof Renal cells or precursors thereof, generated in accordance with a method of the invention may be used to treat kidney disorders or damage, or renal cancer. The cells, or tissue or a functioning kidney regenerated therefrom, may be administered to a patient to treat acute or chronic decline in renal function. Functional renal cells or regenerated kidney can be implanted into the donor of the hematopoietic cells from which the renal cells are derived or into another patient. Renal cells or precursors there of may be used to construct an artificial kidney system (e.g. a system based on a hollow fiber filtration system.

Corneal cells or precursors thereof, generated in accordance with a method of the invention may be used to treat a variety of corneal and/or conjunctival epithelial cell injuries, degenerations and/or abnormalities, including subjects having ocular surface diseases such as Stevens-Johnson's Syndrome, chemical and thermal burns, ocular surface tumors, immunological conditions, radiation injury, inherited syndromes such as aniridia, ocular pemphigoid, macular degeneration, and the like. The corneal cells or precursors thereof may be particularly useful in treating patients where the normal stem cell population of the corneal limbus is depleted, non-functional or otherwise inadequate to promote healing of the corneal damage.

The cells, cell preparations, and cellular compositions of the invention may be used as immunogens that are administered to a heterologous recipient Administration of non-hematopoietic and hematopoietic cells obtained in accordance with the invention may be accomplished by various methods. Methods of administering cells as immunogens to a heterologous recipient include without limitation immunization, administration to a membrane by direct contact (e.g. by swabbing or scratch apparatus), administration to mucous membranes (e.g. by aerosol), and oral administration. Immunization may be passive or active and may occur via different routes including intraperitoneal injection, intradermal injection, and local injection. The route and schedule of immunization are in accordance with generally established conventional methods for antibody stimulation and production. Mammalian subjects, particularly mice, and antibody producing cells therefrom may be manipulated to serve as the basis for production of mammalian hybidoma cell lines.

The cellular compositions of the invention may be used to prepare model systems of disease. The cellular compositions of the invention can also be used to produce growth factors, hormones, etc.

In an aspect the invention provides a culture system from which genes, proteins, and other metabolites involved in proliferation or differentiation of hematopoietic or non-hematopoietic cells can be identified and isolated. The cells in a culture system of the invention may be compared with other cells (e.g. differentiated cells) to determine the mechanisms and compounds that stimulate production of non-hematopoietic and hematopoietic cells.

The cellular compositions of the invention can be used to screen for genes expressed in or essential for differentiation of non-hematopoietic cells. Screening methods that can be used include Representational Difference Analysis (RDA) or gene trapping with for example SA-lacZ (25). Gene trapping can be used to induce dominant mutations (e.g. by deleting particular domains of the gene product) that affect differentiation or activity of non-hematopoietic cells and allow the identification of genes expressed in or essential for differentiation of these cells.

The expanded cell preparations of the invention comprising increased numbers of hematopoietic stem cells and progenitor cells may be used for enhancing the immune system of a patient. The cell preparations will facilitate enhancement or reconstitution of the patient's immune and/or blood forming system.

In an aspect of the invention, the cellular compositions of the invention are used in the treatment of leukemia (e.g. acute myelogenous leukemia, chronic myelongenous leukemia), lymphomas (e.g. non-Hodgkin's lymphoma), neuroblastoma, testicular cancer, multiple myeloma, melanomas, breast cancer, solid tumors that have a stem cell etiology, or other cancers in which therapy results in the depletion of hematopoietic cells.

In another aspect of the invention, a cellular composition of the invention, with or without genetic modification to provide resistance to HIV, is used to treat subjects infected with HIV-1 that have undergone severe depletion of their hematopoietic cell compartment resulting in a state of immune deficiency.

The hematopoietic stem cells and progenitor cells in the expanded cell preparation may also be transfected with a desired gene that can be used for treatment of genetic diseases. Hematopoietic cell-related genetic diseases can be treated by grafting the expanded cell preparation with cells transfected with a gene that can make up for the deficiency or the abnormality. of the gene causing the diseases. For example, a normal wild type gene that causes a disease such as β-thalassemia (Mediterranean anemia), sickle cell anemia, ADA deficiency, recombinase deficiency, recombinase regulatory gene deficiency and the like, can be transferred into the hematopoietic stem cells or progenitor cells by homologous or random recombination and the cells can be grafted into a patient. Further, a preparation comprising normal hematopoietic stem cells and progenitor cells free from abnormalities of genes (from a suitable donor) can be used for treatment.

Another application of gene therapy permits the use of a drug in a high concentration, which is normally considered to be dangerous, by providing drug resistance to normal hematopoietic stem cells by transferring a drug resistant gene into the cells. In particular, it is possible to carry out the treatment using an anticancer drug in high concentration by transferring a gene having drug resistance against the anticancer drug, e.g., a multiple drug resistant gene into an expanded cell preparation comprising hematopoietic stem cells and progenitor cells.

Diseases other than those relating to the hematopoietic system can be treated by using the expanded cell preparations comprising hematopoietic stem cells and progenitor cells in so far as the diseases relate to a deficiency of secretory proteins such as hormones, enzymes, cytokines, growth factors and the like. A deficient protein can be induced and expressed by transferring a gene encoding a target protein into the hematopoietic stem cells or progenitor cells under the control of a suitable promoter. The expression of the protein can be controlled to obtain the same activity as that obtained by the natural expression in vivo.

It is also possible to insert a gene encoding a ribozyme, an antisense nucleic acid or the like or another suitable gene into the hematopoietic stem cells or progenitor cells to control expression of a specific gene product in the cells or to inhibit susceptibility to diseases. For example, the hematopoietic stem cells and progenitor cells can be subjected to gene modification to express an antisense nucleic acid or a ribozyme, which can prevent growth of hematic pathogens such as HIV, HTLV-I, HTLV-II and the like in hematopoietic stem cells or cells differentiated from hematopoietic stem cells.

The cell preparations comprising hematopoietic stem cells and progenitor cells can be introduced in a vertebrate, which is a recipient of cell grafting, by, for example, conventional intravenous administration.

The invention also relates to a method for conducting a regenerative medicine business, comprising: (a) a service for accepting and logging in samples from a client comprising hematopoietic cells capable of forming cells that have the potential to form hematopoietic and non-hematopoietic cells; (b) a system for culturing cells dissociated from the samples, which system provides conditions for producing cells that have the potential to form hematopoietic and non-hematopoietic cells; (c) a cell preservation system for preserving cells generated by the system in (b) for later retrieval on behalf of the client or a third party. The method may further comprise a billing system for billing the client or a medical insurance provider thereof.

The invention features a method for conducting a stem cell business comprising identifying agents which influence the proliferation, differentiation, or survival of cells that have the potential to form hematopoietic and non-hematopoietic cells. Examples of such agents are small molecules, antibodies, and extracellular proteins. Identified agents can be profiled and assessed for safety and efficacy in animals. In another aspect, the invention contemplates methods for influencing the proliferation, differentiation, or survival of cells that have the potential to form hematopoietic and non-hematopoietic cells by contacting the cells with an agent or agents identified by the foregoing method. The identified agents can be formulated as a pharmaceutical preparation, and manufactured, marketed, and distributed for sale.

In an embodiment, the invention provides a method for conducting a stem cell business comprising (a) identifying one or more agents which affect the proliferation, differentiation, function, or survival of cells that have the potential to form hematopoietic and non-hematopoietic cells of the invention; (b) conducting therapeutic profiling of agents identified in (a); or analogs thereof for efficacy and toxicity in animals; and (c) formulating a pharmaceutical composition including one or more agents identified in (b) as having an acceptable therapeutic profile. The method may further comprise the step of establishing a distribution system for distributing the pharmaceuctial preparation for sale. The method may also comprise establishing a sales group for marketing the pharmaceutical preparation. The invention also contemplates a method for conducting a drug discovery business comprising identifying factors that influence the proliferation, differentiation, function, or survival of cells that have the potential to form hematopoietic and non-hematopoietic cells of the invention, and licensing the rights for further development.

Having now described the invention, the same will be more readily understood through reference to the following examples which are provided by way of illustration, and are not intended to be limiting of the present invention.

EXAMPLE 1

Materials and Methods

Maternal Blood Screening:

Maternal blood was screened for HIV I/II, HTLV-I/II, Hepatitis B (HBs Ag), Hepatitis C (anti HVC), CMV and VDRL at the time of registration prior to 34 weeks gestation. Written consent for collecting and processing umbilical cord blood was obtained at the time of registration. Qualified hospital personnel, following protocols approved by the human ethics committee of the Toronto General Hospital and the University of Toronto, collected the cord blood at the time of delivery.

Sample Processing:

The blood volume was reduced and the red blood cells removed with either Ficoll or Pentaspan (starch) treatment Samples were collected using 60 ml syringes containing the anticoagulant, Acid Citrate Dextrose (ACD) at 1 ml per 10 ml of blood (10% v/v) or collected directly into a 250 ml blood bag (Baxter-Fenwal, Deerfield, Il, USA) and Penicillin G was added directly to the bag. Ficoll (Histopaque-1077, Sigma, St. Louis, USA) gradient centrifugation was used to obtain an enriched population of mononuclear cells. Briefly, blood was diluted 1:1 with RPMI medium and 30 ml was overlaid on a 15 ml cushion of Ficoll (1.077). The gradient was centrifuged at 300 g for 30 min at room temperature and the layer of mononuclear cells (MNC) was collected. The Ficoll layer below was also collected. The MNC and the Ficoll layer were both resuspended in 2× volume of wash solution (12.5 ml filtered plasma from the donor cord blood, 120 ml Iscoves modified Dulbecco medium, 3 ml ACD). The sample was centrifuged at 300 g for 10 minutes at room temperature. Cell pellets were collected and combined.

Original volumes of the umbilical cord blood sample included the 10% v/v of ACD. Therefore a 100-ml volume included approximately 90 ml of blood and 10 ml of ACD.

For starch processing, 1 ml of starch (Pentaspan, Dupont, Ill. U.S.A.) is added to 5 ml of blood, mixed, then centrifuged for 10 minutes at 50×g. The leukocyte rich upper layer is collected and the cells are pelleted by spinning at 400×g for 10 minutes. The pellet is resuspended in 5 ml of IDM and 6 volumes of red cell lysis buffer (Ammonium Chloride Buffer). After 10 minutes at room temperature the cells are pelleted and washed 1× in PBS and either cryopreserved or resuspended in column buffer.

Cryopreservation:

All steps were performed on ice. The cell pellet was resuspended in IMDM/10% autologous serum or FBS/10% DMSO. Up to 6 aliquots were frozen per sample by placing the sample in Nalgene cryovials (Nalgenenunc, Rochester, N.Y.) in a −80° C. freezer overnight. For long term storage, samples were moved to liquid nitrogen (−196° C.).

Isolation of an Enriched Stem Cell or Progenitor Cell Population.

Different methods using two different columns were used for the isolation of stem or progenitor cells.

A. MACS column (Mitenyl Biotech., Germany). A positive selection magnetic column using a monoclonal antibody (Mab) to CD34. The MAb once bound to the cell is bound to a metal bead and is subsequently retained on the column, which is attached to a magnet. All of the other cells are washed of the column. The column is removed from the magnet and the CD34+ cells are eluted.

B. Stem Sep column (Stem Cell Technologies) is a negative selection column and is better suited for the isolation of primitive stem cells. Since all stem cells may not be CD34+ (26) a negative selection column removes all known, unwanted cells, leaving behind an enriched stem cell population. The antibody cocktail removes all mature lymphoid and myeloid cells are removed as well as all late progenitor stage cells. It contains a set of lineage specific surface markers found on mature hematopoietic cells; CD2, CD3, CD14, CD16, CD19, CD24, CD56, CD66& GLYCOPHORIN A.

C. Cell Culture Systems:

A variety of cell culture systems were tested. A number of media were tested and the main components areas follows;

A. Conditioned medium: Human embryonic fibroblasts (HEF-CM) grown in αMEM with 20% FBS (fetal bovine serum) for 72 hours. The medium is removed and the cells and debris is removed with centrifugation and filtering (0.22 µM filter). The medium is stored at −20° C.

B. Non conditioned medium/serum free: IMDM, 1% bovine serum albumin, 10 βg/ml bovine pancreatic insulin, 200 µg/ml human transferring, $10^{-4}$M β-mercaptoethanol, 2 mM L-glutamine and 40 µg/ml LDL (Low Density Lipoproteins).

C. ES cell medium without LIF in the presence of mitomycin treated human embryonic fibroblast cells.

Cells were grown in any one of the three media with or without the following growth factors in any combinations; 25-100 ng/ml FGF-4, 25-100 ng/ml FGF-2, 25-100 ng/ml IL-3, 25-100 ng/ml SCF, 25-100 ng/ml FLT3 ligand, 25-100 ng/ml TPO, 25-100 ng/ml GM-CSF, 25-100 ng/ml IL-6, 25-100 ng/ml NGF.

Cells were grown for 4 days to 76+ days in the medium with medium changes and growth factor changes either weekly, twice weekly, or thrice weekly. All cells were grown in NUNC brand tissue culture treated 6, 12 or 24 well plates (Becton Dickinson, N.J., USA).

Flow Cytometry Analysis: Cell Number and Viability.

Samples were stained for various cell surface markers (Becknan-Coulter) and subjected to flow cytometer analysis; Coulter-Epics (Coulter. Burlington, Canada). Isotype controls were used in all cases. All samples were labelled for 10-20 minutes at 4° C., washed and fixed in 10% formalin, as per manufacturer's instructions.

Colony Forming Units Plating Assay

A pre-made methyl cellulose based colony assay medium (Stem Cell Technologies)was used. The medium is formatted to grow primitive progenitors (cat# H4435). Cells were plated at 500 CD34+ cells per 3 ml of medium or 1500-3000 cells per 3 ml of medium for non-selected cells. All populations were plated in duplicate and scored at day 12, 14, 16 and 18.

LTC-IC Assays.

Cells were also grown in Long Term Culture-Initiating Cell assays that allow for the growth of early hematopoietic progenitor cells. This assay links the CFU-assay and the NOD/SCID assay. Cells are grown on feeder cells which allow for the long term growth of hematopoietic cells.

Column Re-Selection

For some experiments the cells were re-selected using the Stem Sep column (Stem cell Technologies). Tissue culture cells were labeled with the appropriate antibody cocktail and passed through the column as described above. Output cells were deemed to be negative for the surface markers targeted in the cocktail and these cells were either checked for positive surface markers by flow cytometry, placed in CFU-assays, replated for continued tissue culture or used to engraft NOD/SCID mice.

NOD/SCID Mouse Engraftment

Non Obese Diabetic/Severe Combined Immune Deficient (NOD/SCID) mice were used to test the engraftment potential of the human umbilical cord blood stem cells. All experiments followed established protocols and received animal ethics approval. NOD/SCID mice were maintained in a clean room in isolator racks and given food and water. The mice were irradiated 2 hours before engraftmnent at 360 Rads using a $Cs^{137}$ source. The mice were then injectedby tail vein with 200 µl of cells. Mice were given an i.m injection of antibiotics and monitored daily. Survival rate was 80+% per experiment. At 2 weeks, 4 weeks, or 6 weeks, animals were sacrificed by cervical dislocation. Femurs were removed and the bone marrow flushed. Cells were washed in PBS and the cell pellet was subjected to Red Cell Lysis Buffer for 3 minutes and washed again. Cells were either cryopreserved for re-engraftment, analysed by flow cytometry, or subjected to RNA isolation for PCR analysis or DNA microarray analysis.

Liver, spleen, muscle and brain tissue were also isolated. Tissues were divided into pieces and fixed in 4% paraformaldehyde followed by embedding in paraffin wax. Some of the tissue was separated into single cell suspension using a mild trypsin treatment (27) and labeled with fluorescent antibodies as described above.

Immunohistochemistry and Immunocytochemistry

All tissues were fixed in 4% paraformaldehyde followed by washes in PBS. The tissue was dehydrated followed by embedding in paraffin wax. 6µm sections were cut and placed on glass slides. Slides were dewaxed and subjected to antibody. staining with fluorescent tagged antibodies. Slides were analyzed on a deconvolution microscope.

Osteoclast:

Osteoclast formation was accomplished by culturing the cells in IMDM+10% serum+GM-CSF. Positive cell activity was determined by plating the cells on calcium citrate substrates and measuring loss of the substrate as active osteoblasts absorb the bone like substrate.

TRAP'Staining:

TRAP Staining was carried out as described in Minkin Cedric (28). Cells were grown for various periods in either 96-well or 24-well plates under the influence of several "factors". Tartate resistant acid phosphatase staining was carried out on cells as follows:

6.4 ml of naphthol-as-Bi-phosphoric acid (12.5 mg/ml in dimethylformamide).
6.4 ml acetate solution (2.5 mol/L) pH=5.2
3.2 ml Tartrate solution (0.67 mol/L) pH=5.2
Fast Red TR (0.1 g)
64 ml of Distilled water The above solutions were mixed and filtered. Cells were then incubated for 45 minutes at 37° C.

Resorption Studies:

Cells were grown for 3 weeks under conditions that are favourable for TRAP positive 10,000 cells were seeded on to osteologic slides and grown for 2 weeks with media changes every two to three days. Media consisted of IMDM and GM-CSF with serum. At 10 and 14 days the experiment was stopped and Von Kossa staining was carried-out.

Ultrastructural Studies:

Cord blood cells were grown under above conditions for 21 days in 24-well plates. Cells were then scraped off and centrifuged in a microtube at 600 g for 5 minutes. Re-suspension in 2% gluteraldehyde for 1 hour followed by transfer to cacodylate buffer and subsequent processing for viewing under electron microscopy.

Endothelial;

Cells are grown in culture dishes or chamber slides as well as 3-D cultures which allow for the formation of capillary networks. For cultures on chamber slides, cells are plated in M119 medium with serum (10%), supplemented with endothelial growth factor supplement (Sigma). Cells are fed twice per week by the removal of medium without the loss of cells. Capillary formation is accomplished by placing 2,000-10,000 cells in 5 µl volumes on a 0.5 ml matrix made by mixing 0.5 ml of 3 mg/ml fibrinogen in M199 medium with 10 µl of thrombin (µg/ml) and then covering the cells with a second 0.5 ml of matrix in a 24 well plate and covering with 1 ml of M199 +5% serum. Medium is changed once per week for 3-4 weeks until endothelial cell networks develop.

Adipocytes:

Sudan IV staining was carried out to determine whether there is presence of fats in the cells grown under the conditions described above. Briefly cells were fixed in 70% ethanol for 5 minutes followed by incubation with a solution of Sudan IV (2 g/ml in 50:50 acetone:ethanol) for another 5 minutes. Cells were then washed with 70% ethanol and then viewed under a microscope.

Osteoblast:

α-MEM with $10^{-8}$M Dexamethasone, 10 mM β-glycerolphosphate, 0.2 mM Ascorbic Acid; 10% Serum. Cells were grown for 3-4 weeks. For Alzirin Red staining, cells are fixed in 70% ice cold ethanol for 30 minutes, then stained for 10 minutes with 40 mM Alzirin red (pH 4.0).

Neural:

Cells were placed into DME+10% serum and grown for 3 weeks with twice weekly media exchanges. Some cultures were supplemented with 10-50 nanomolar Retinoic Acid.

Muscle:

Cells were grown in FGF, SCF, FLT3Ligand in Stem Span medium (Stem Cell Technologies) for 2-21 days. At any time point the cells were either transferred into 20% serum in DME (high glucose) for three weeks in order to produce mesenchymal cells or transferred directly to various medium at 37° C. or 33° C. or 6% Oxygen (37° C.) in one of the five listed conditions:

A: αME+10% serum+50 µM 2-mercaptoethanol
B: αMEM+10% serum+50 µM 2-mercaptoethanol+5-Azacytidine
C: αMEM+10% serum+50 µM 2-mermaptoethanol+10 µg/ml insulin +0.1-1 µM Dexamethasone+0.5 µM isomethylbutylxanthine
D: αMEM+10% serum+Chick embryo extract (5%)
E: αMEM+1% serum+Chick embryo extract (5%)

Cells were cultured for 2-4 weeks and tested for muscle specific markers by PCR and immunocytochemistry.

Hepatocytes:

Livers were isolated from mice that received cells through tail vein injections. Upon sacrifice, the livers were quickly removed and either fixed in 10% formalin and processed with paraffin wax for imunohistochemistry or single cell suspensions were produced and cells were stained with anti-HLA-ABC antibody and anti-CD45 antibody.

Results:

In all experiments lised below, cells were isolated from human umbilical cord blood. starting populations of cells were tested 1) unfractionated leukocytes 2) lineage minus cells (CD2, CD3, CD14, CD16, CD19, CD24, CD56, CD66& GLYCOPHORIN A minus). Lineage minus cells are obtained by initially removing known mature blood cells thereby leaving behind immature cells and cells lacking any known blood marker(unidentified cells). This population of lineageminus cells is HLA-ABC positive, CD45$^+$ (100%), and enriched for CD34 (50-80%), CD38 (50-80%), and CD33 (50%), a myeloid marker and 3) Lineage positive cells. In summary, but detailed below, the key population is the lineage minus population because in the majority of studies lineage positive cells failed to show any stem cell properties, and the frequency of cells with stem cell potential found in the unfractionated cell population suggests they are from the lineage minus population contained within.

The Appearance of Non-Blood Cells

Non-blood cells were produced from CD45$^+$ UCB cells. First, it was observed that a combination of prolonged culturing with reduced feedings caused the differentiation of these cells by letting them withdraw from the cell cycle. The cells begin to adhere resulting in mixed colonies of elongated adherent cells and loosely attached to them are round cells. As long as FGF is present the cells can maintain these colonies, which appear at about three weeks of culture. After three more weeks the round cells begin to die and the adherent cells stop dividing but remain alive. The cells stained positive for the mesenchymal marker, vimentin. After 6-10 weeks in culture (total time) the adherent cells persist and show morphologies resembling endothelial cells, adipocytes (fat), and osteoclasts. These specialized cells occur infrequently. By altering the culture conditions (as mentioned above and detailed below) the fate of the cells can be better controlled. Initial studies were performed in order to determine the optimum cytokine type and concentration required to promote stem cell growth. The goal was to produce a proliferating population of cells that does not require serum, conditioned medium or feeder cells in order to maintained multi-potential cell properties as defined by the ability of the cells to give rise to mature hematopoietic and non-hematopoietic cells and tissues. It is important to eliminate both the requirement for serum and conditioned medium as this is not feasible for a clinical setting. Furthermore, reducing the dependence on serum and conditioned medium provides us with more control over the maintenance of cell phenotype and cell proliferation.

Mesenchymal-like cells can be directly obtained by plating whole cord blood directly into DME or IMDM plus 10-20% serum. (See below mesenchymal cell intermediate).

Figure 1:
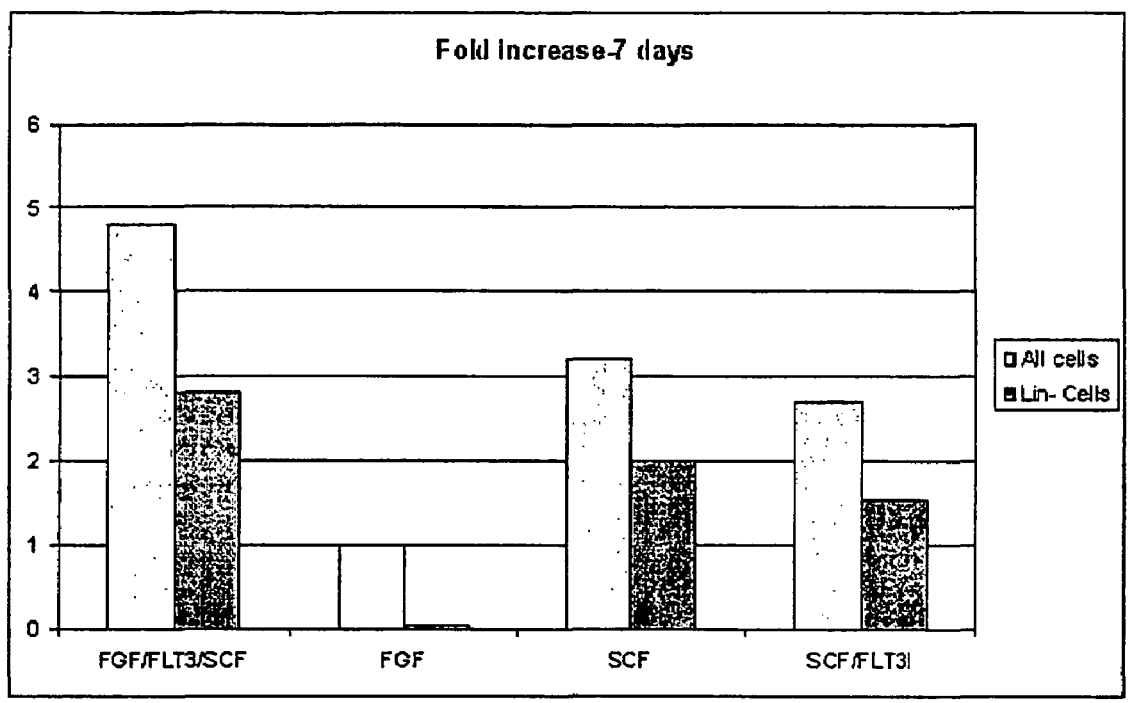
FIG. 1 shows the growth and maintenance of $Lin^-$ stem cells. There was an increase in $Lin^-$ stem cells after 7 days growth with different growth factors. $Lin^-$ cells were grown in serum free medium with combinations of FGF-4, SCF and Flt-3 ligand. The best growth and maintenance of stem cells occurs when all three growth factors are present.

Cytokine Supplementation:

Leukocytes from umbilical cord blood cells were depleted of all mature cells leaving an enriched stem and progenitor cell population. These cells can be maintained in serum free conditions with growth factor supplementation for approximately three months, although the majority of cell proliferation occurs in the first 28 days then tapers off. Cultures can be maintained in a highly proliferative state by feeding every 48 hours and separating the lineage minus cells from the lineage positive population as done at the beginning of the culture period every 7-10 days or on a continuous basis. FGF-2 and FGF-4 were focused upon due to their ability in the murine embryo to maintain proliferation of non-differentiated cells. Furthermore, FGF-2 and FGF-4 are down regulated prior to cells undergoing differentiation, thus making it an ideal candidate for stem cell proliferation. FGF-2 and FGF-4 were tested in conjunction with +/− serum, +/− cytokines, on different substrates . The studies showed no difference between FGF-2 and FGF-4. However, FGF-4 alone was used because of its use in maintaining human embryonic cell lines. The addition of SCF and FLT-3ligand to the FGF-4 containing medium increased the proliferation rate. FGF, SCF or Flt-3ligand used alone in serum free conditions resulted in reduced cell proliferation, while combinations of these cytokines resulted in improved yields of stem cells. SCF had a minor effect on cell proliferation rates when added to FGF, Flt-3ligand cultures, but was critical in blocking differentiation of the stem cell pool (FIG. 1).

The frequency of FGF supplementation, but not the concentration, greatly affected the outcome of the cultures. 100 ng/ml and 25 ng/ml of FGF-4 or FGF-2 were tested with 25 ng/ml of FLT-3 ligand and 25 ng/ml of SCF. There was no difference in the cell proliferation rate, the frequency of CD34$^+$/CD38$^-$ cells or CFU's when the supplementation schedule was kept constant. This is due to the rapid degradation rate of FGF. Once per week feeding for 4 weeks resulted in maintenance of some cells with HSC characteristics but the majority of cells differentiated and died. Interestingly FGF-4, FLT-3L, SCF, serum free, with once/week media changes resulted in massive cell proliferation for three weeks, followed by the majority of cells dying with the remainder forming mixed colonies of round, non- adherent and elongated adherent cells of equal proportions. Feedings of about 3 times per week are required to maintain high proliferation levels and maintenance of the stem cell phenotype. Furthermore, reselection of the cells at weekly intervals through the same negative selection column helped to maintain and expand the lineage minus population. By supplementing the cultures with growth factors three times per week the cells were maintained as round, non-adherent cells. The cells have been maintained in this state for about 80 days before terminating the experiment.

Other Cytokines:

Although some cytokine supplementation protocols tested resulted in massive proliferation the rate of differentiation was also high resulting in a decreased number of stem cells of the total cell population. IL-3 with Flt-3 and SCF resulted in massive cell proliferation but the lineage minus population was lost as they differentiated rapidly. TPO with Flt-3 and SCF resulted in a better balance of cell proliferation and stem cell maintenance. NGF, SCF and FLT-3ligand also gave similar results to FGF. TPO, SCF & FLT3ligand cultured cells were also compared to FGF, SCF, FLT3ligand cells. Although the TPO treated cells proliferate much better than FGF cells (12-20 fold increase vs. 4-10 fold), TPO cells have a more limited range of producing non-hematopoietic lineages.

Formation of Non-Hematopoietic Cells is not Dependent on a Mesenchymal Cell Intermediate.

The adherent cell population that appeared with infrequent feedings or as a result of growing unfractionated cord blood cells in serum conditions, is reminiscent of the mesenchymal cell population found in bone marrow aspirates. First it was investigated whether the adherent stage of growth observed in the original population was a mesenchymal cell population similar to that found in bone marrow, and 2) a mandatory step towards non-blood differentiation. Jiang et al (29) reported a $CD45^-$ (non-blood), mesenchymal cell population isolated from bone marrow that is capable of producing a wide range of cell types from a clonal cell population. We tested 1) Lineage negative cells (stem and progenitor cells), 2)Lineage positive cells (mature blood cells) and 3)unfractionated UCB cells were tested.

Figure 2:
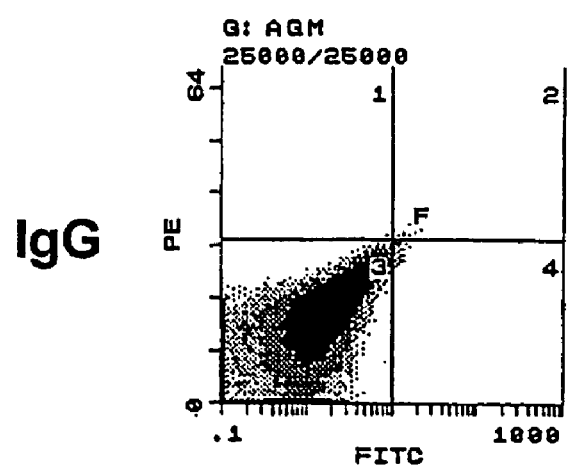
FIG. 2 shows that the $Lin^-$ stem cells are $HLA-ABC^+$ and CD45. $Lin^-$ cells were selected and analyzed by flow cytometry for CD45 and HLA-ABC positive cells. Day 0 Lin– cells and the same cells grown for 7 days are 100% $CD45^+$ and $HLA-ABC^+$. Day 0 $Lin^-$ cells contain two populations of $CD45^+/HLA-ABC^+$ cells with one expressing lower levels, but still clearly positive.
Figure 2:
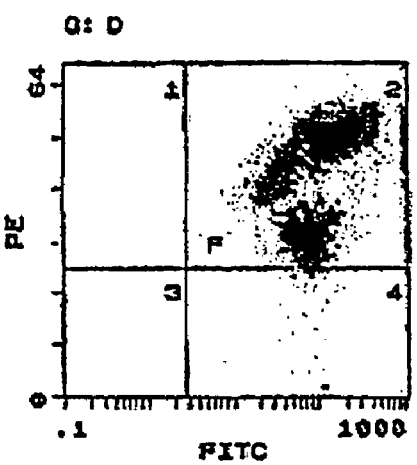
Figure 2:
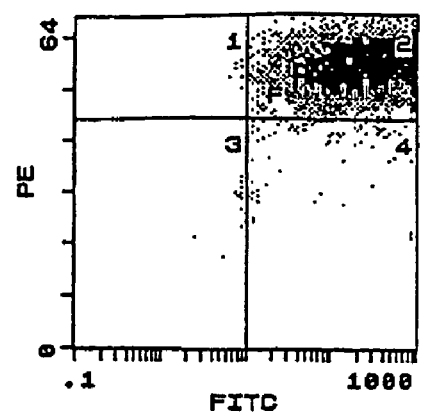

Lineage Negative Cells:

UCB Lin− cells were grown in SCF and FLT-3 ligand with or without FGF-4. After three weeks of growth, mixed colonies appear that consist of stromal like cells and round hematopoietic cells. Cells grown in FGF-4, SCF, Flt3ligand, produce a greater number of these colonies. Furthermore, if the cells are fed at 2-3 feedings/week versus once/week the cultures contain more non-adherent single cells. These round, non-adherent cells are still capable of forming mesenchymal cells once the growth factors are reduced or the cells are placed into serum containing medium. Growing the cells in FGF, SCF and Flt3ligand allows an increase in the number of cells with mesenchymal cell properties. Since the mesenchymal like cells appear after three weeks of growth, the round non-adherent cells that dominant the cultures in the first 2-3 weeks were tested. The expanded, non-adherent cells contain the ability to generate specific non-hematopoietic cell types (as described in Materials and Methods and below). Therefore with frequent feedings the cells tend to remain non-adherent and retain their potential for producing non-hematopoietic cells. Furthermore the round, non-adherent cells remain $CD45^+$ and HLA-class $I^+$ (FIG. 2).

Figure 3:
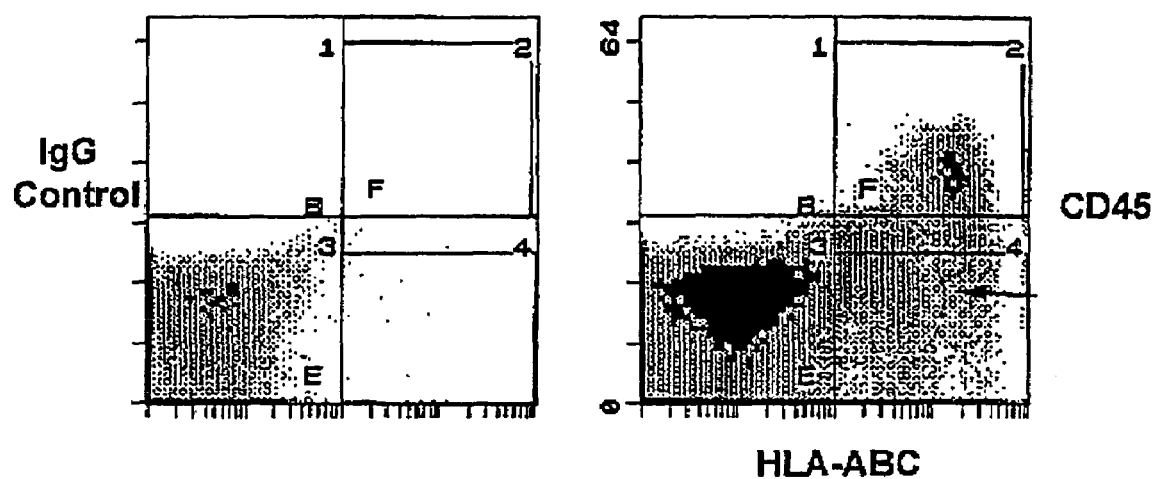
FIG. 3 shows the presence of human stromal cells in engrafted NOD/SCID mice. $CD45^-/HLA-ABC^+$ cells were isolated from bone marrow aspirates from NOD/SCID mice engrafted with FGF, SCF, FLT-3 ligand cells or day 0 $Lin^-$ cells. These cells may be stromal-like cells. This supports the observation of stromal/mesenchymal cells in the cultures.

If the UCB lin cells were placed directly into conditions which promote the growth of adherent, mesenchymal-like cells (DME +20% serum) the cells would die after one week. When the lin cells were grown for 8 days in FGF-4, SCF, Flt3ligand prior to culture in serum medium, vimentin positive cells would develop. These cells could be maintained in serum conditions for ~6 weeks. Furthermore, these cells lost their ability to produce positive blood forming cells when tested in CFU assays and LTC-IC in vitro assays. These cells also died when placed in cultures that promote endothelial cell development (VEGF containing cultures) or osteoclasts. Interestingly, FGF-4, SCF, Flt3ligand grown cells placed into DME +10% serum would be 50% positive for the neural marker, neurofilament. Therefore conditions which lead to vimentin positive cells also give rise to neural cells. For muscle and bone, placing the cells from FGF-4, SCF, Flt3ligand cultures, directly into growth conditions which cause tissue specific differentiation, would result in positive cells for the specific tissue tested. UCB Lin- cells placed directly into bone or muscle differentiating medium would die. An increase in muscle and osteoblast precursor cells would occur when the cells were first grown in FGF-4,SCF, Flt3ligand medium and then DMEM or IDMM plus serum (10-20%) for 14days. Stromal/Mesenchymal like cells have also been identified from UCB in vivo. Lineage depleted UCB cells (UCB Lin−) were injected into NOD/SCID mice. Upon analysis of the bone marrow of the mouse after 10 weeks, stromal and hematopoietic cell populations were identified. CD45 is a pan human leukocyte marker and HLA-ABC is a pan human cell marker. Cells that are HLA-ABC positive and CD45 negative are human, non-blood cells, and most likely stromal cells (FIG. 3).

Lineage Positive ($Lin^+$):

These cells were grown in identical conditions as the $lin^-$ cells and tested for the presence of adherent cells as well as non-blood markers. The majority of $lin^+$ cells died (95%) within 7-10 days of culture. Surviving cells produced in a minority of adherent cells (1/1,000,000 cells) which failed to divide and died. Lineage positive cells grown in tissue specific medium resulted in the death of all cells. This indicated that the cells removed (CD2, CD3, CD14, CD16, CD19, CD24, CD56, CD66& GLYCOPHORIN A positive cells) are not capable of producing non-hematpoietic cells.

Non-Fractioned:

Cells were placed directly into 20% serum/DME or IMDM. The frequency of adherent cells was 10/100,000. These cells proliferated slowly for 6 weeks then died. Interestingly the best yield of adherent cells came when the non-adherent, non-fractioned cells cultured in DME or IMDW/ 10-20% serum for 4 days were transferred to a new culture chamber with fresh medium. Within 24 hours of transfer, 10% of the cells adhere. The few non-adherent cells left in the original well died. After 46 weeks in culture the number of live adherent cells was similar to the number adherent cells from the Lin- cell fraction grown for the same length of time, strongly suggesting that the active, key cell is found in the lineage negative population. The adherent, non-fractionated cells are vimentin positive and have identical properties to that of the Lin- adherent cells.

Lineage + and unfractioned cells were also grown in FSF cultures for 7 days prior to the above tests. No differences in the results were observed when compared to not pre-culturing in FGF-4, SCF, Flt3ligand medium. Any effect on the lineage negative cells contained within the unfractionated cells would be masked by the large number of non-reactive lineage positive cells. Therefore, F FGF-4, SCF, Flt3ligand growth period has a unique effect on Lineage minus cells.

It was previously reported that NGF-receptor is expressed on mesenchymal and some blood cells in the bone marrow. Isolation of NGF-$R^+$ cells from the bone marrow is enriched for mesenchymal cells capable of developing into osteoblasts and fibroblasts (30). FACS-sorting of a NGF-R$^+$ population from human UCB did not result in cells with mesenchymal properties. Cells were isolated and grown in conditions that are conducive to mesenchymal cell growth. The positive cells did not survive well in these cultures and never adhered as expected. Although not tested, the cells are probably the blood cell NGFR positive population.

How Early do the UCB Cells Begin to Display Non-Hematopoietic Markers?

The observation that UCB cells grown in serum conditions can give rise to vimentin positive cells and cells that morphologically resemble non-blood types prompted testing of UCB cells at different; stages of growth for the expression of non blood markers. Day 0 lin$^-$ cells were negative for all non-blood, markers tested. Since adherent cells do not appear until day 21 of culture in FSF medium, the ability of non-adherent, early stage cells at day 2, 4, 8, 14 and 21 were tested. In these cultures after at least 4 days (one-two cell divisions), non-hematopoietic embryonic and early tissue specific markers arise.

Lineage negative and positive cells as well as non-selected cells were tested. Cells were either moved directly into tissue-specific in vivo and in vitro assays that enabled determination of their developmental potential for blood and non-blood cells, or the cells were first cultured under conditions which, depending on the growth factor used, may allow for an increased capacity of the CD45+ population to grow into non-blood cells.

A combination of PCR analysis, antibody staining, enzymatic assays and in vivo functional assays was used to test the non-hematopoietic potential of UCB cells. Day 0 Lin$^-$ cells are negative for non-blood markers but 100% positive for HLA-ABC and the blood marker CD45. Differentiation of cells into non-blood cells was a two-stage process. The first stage required growing UCB lin$^-$ cells in FGF-4,SCF, Flt3ligand for a minimum of 4 days or in 10-20% serum in DMEM or IMDM as outlined above.

PCR analysis and protein detection with antibodies to non-blood markers showed that day 0 lin$^-$ cells are negative for nestin (neural), Desmin, Cardiomyosin (muscle), GFAP (astrocyte) FLK-1 (mesoderm and endothellal), CBFα-1 (bone) and Oct4 (embryonic stem cell) by PCR. The same cells are negative by antibody for FLK-1, CD31 (endothelial), Oct-4, Neurofilament, Nestin, Parkin (neural), GFAP (astrocyte), Cyp1A2 hepatocyte),CBFα-1 (osteoblast),Desmin, MyoD and muscle actin (muscle).

Cells were also negative for TRAP and calcium citrate substrate resorption (osteoclast), negative fbr calcium deposits by Aizirin red staining (osteoblast) and Sudan IV staining (adipocytes). Although day 0 lin$^-$ cells are enriched for CD34, a surrogate marker for hematopoietic stem cells, these observations indicate that there is no relationship between CD34 and the appearance of multipotent stem cells. During the culture period in cytokine supplemented, serum free medium, CD34 cells increase in frequency along with the appearance of multipotential stem cells (UCB stem cells) but the UCB stem cells are also found in the CD34$^-$ population. The CD38 marker is lost within the first 4 days and CD33 appears during this time. By day 8 greater then 80% of the cells are CD33$^+$ but this exceeds the number of UCB stem cells.

Cells were grown for 2, 4, 8, 14 and 21 days in FGF-4, SCF, Flt3ligand fed 3×/week. Day 2 cells remained negative for the same PCR markers while cells grown for 4 days or more expressed nestin, desmin, GFAP, Flk-1 and Oct-4. The presence of Oct-4is highly significant as it is considered a marker of stem cells. To explore this further UCB lin– cells were grown in IL-3 with SCF and Flt-3 ligand, Neural Growth Factor with SCF and Flt-3 ligand or TPO with SCF and Flt3-ligand. IL-3 supplemented cultures grew rapidly but were negative for Oct-4, desmin, nestin. NGF supplemented cultures were positive for only OCT4. TPO-cultured cells at day 8 are negative for nestin and FLK-1, positive for OCT4 and weak to negative for Desmin by PCR. Thus demonstrating a reduced multipotency when compared to FGF cells.

This is an important observation because OCT4$^+$ or FLK1$^+$ cells are probably an important intermediate cell type (eg; all mature endothelial cells grown are direct derivatives of the FLK1$^+$ population), OCT4 or FLK1 positive cells are not found in the starting population. Therefore, the cell population found in UCB capable of multipotencyis a CD45$^+$/HLA-ABC$^+$/FLK1$^-$/OCT4$^-$ cell. Since UCB stem cells respond well and their appearance in the cultures are dependent on FGF, SCF and Flt-3 ligand the key cells are also FLT3 receptor (member of the receptor tyrosine kinase class III receptors), SCF receptor (c-Kit), and FGFRII positive.

After 2-4 days of growth the cells are positive for non-blood embryonic markers from a wide variety of tissues. In order to further differentiate these cells they had to be placed into tissue-specific cell cultures. The cells are capable of giving rise to multiple blood and non-blood cell types.

In summary, although lineage minus cells in culture will give rise to lineage positive (mature blood) cells, they also give rise to a novel cell type, not found in the original population, that will produce non-blood lineages. These cells seem to be a product of culture conditions as untreated, day 0 lineage minus cells are negative for all non-blood indicators.

These cells could be further differentiated when placed into specific culture conditions that promote the production/ growth of a specific cell type (e.g. osteoclast). Therefore, the cells do not have to go through an adherent phase and the production of vimentin positive cells is not a required intermediate step but it is mandatory that the cells grown in serum free culture in order to allow for the development of non-hematopoietic lineages.

Blood

Despite the fact that that Fgf, Scf, Flt31 cells are able to express non-blood markers, they still maintain their ability to express blood markers. The cells from the umbilical cord are collected in a manner used to isolate cells capable of reconstituting the blood lineages. Growth and proliferation of a stem cell population capable of forming non-blood cells should also maintain its ability to form blood cells. Hematopoietic stem cell maintenance and proliferation was tested using in vitro and in vivo assays. Colony forming unit (CFU) assays, LTC-IC and cell surface marker analysis were used to indicate hematopoietic stem cells. In subsequent experiments NOD/SCID assays were used to verify stem cell phenotype and the ability of these cells to engraft the bone marrow.

Figure 4:
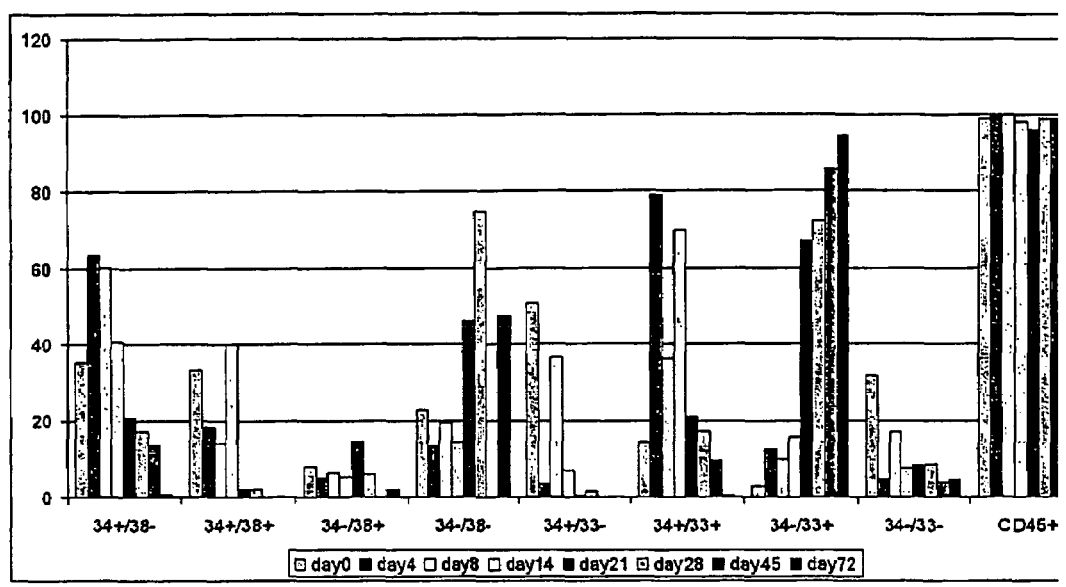
FIG. 4 shows the changes in cell population with time in culture. Initial increases in $CD34^+$ cells occur in the first 2-3 weeks of growth but then decline. $CD33^+$ cells increase rapidly suggesting that existing cells begin to express this marker. A high proportion of cells is $CD45^+$.

Using the above serum free/conditioned medium-free media outlined above that resulted in an increase of cells expressing non-blood markers, an increase in CFU's and LTC-IC was also observed over the first 8 days in culture. Surface analysis of cells grown in Fgf, SCF, Flt3ligand for 4-8 days resulted in a shift in the population from a predominantly CD34+ to a CD33+ population. There was also an increase in CD34$^-$, CD38$^-$, and CD33$^-$ cells. All cells maintained CD45$^+$. Cells were maintained for up to 80 days but in most cases there were few cells left to analyze. Cells never lost their CD45 marker and in some cases where there was CD45$^{lo}$ or CD45$^-$ cells in the initial population, these cells either died or turned on CD45 by day 8 as 100% of the population is positive (FIG. 4).

Figure 5:
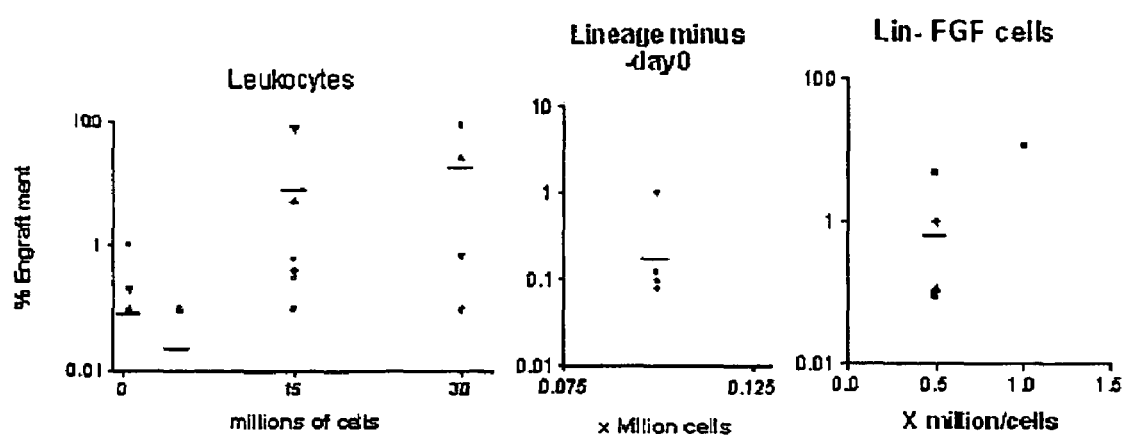
FIG. 5 shows the results for transplanting NOD/SCID mice with cells grown in Fgf, SCF, FLT3 ligand for 8 days. Expansion of the cells is 3× input Transplanting the same number of cells per mouse resulted in comparable levels of engraftment.

In vitro studies clearly show an increase in hematopoietic stem cell numbers during an 8 day+ culture period. In order to address the engraftment potential of the in vitro expanded stem cells, freshly isolated cord blood mononucleated cells, freshly isolated Lin– cells, or in vitro grown cells, were used to. engraft irradiated NOD/SCID mice (FIG. 5). An increase in input cells resulted in an increase level of engraftment Furthermore, an equal number of Lin– placed in culture for a minimum of 8 days had the same engraftment potential as their day 0 counterparts suggesting that more NOD-SCID repopulating cells were produced over the 8 days.

Endothelial Cells, Bone (Osteoclast and Osteoblast), Adipocytes, Muscle, Astrocytes and Neural Cells from Cord Blood Cells:

The cells were plated and maintained (with constant splitting of cultures) at very low densities, which allows single cells to be observed. Stromal like cells (adherent, flat cells) were not observed in the cultures until 3-4 weeks of growth. Round cells (individual cells are pinpointed in a dish for repeated observation) were observed becoming more adherent after 3 weeks of growth. The cells flatten out and their progeny produce both round and flat cells forming a mixed colony. Furthermore, cells maintained in suspension for up to 12 weeks remained alive and non-adherent Aliquots that were removed at one week intervals and allowed to settle and became adherent Conversely, adherent cells could be trypsinized and returned to suspension cultures and continue to grow as non-adherent cells.

Adherent cultures grown for up to 12 weeks in low growth factor serum free medium resulted in cell morphologies reminiscent of fat cells, endothelial cells and osteoblast cells. These cells appeared at low frequencies with all three types appearing in single cultures. In order to determine the identity of these cells the culture conditions were optimized to increase the yields of these cells to the point where enough could be obtained for analysis. As mentioned above, cells grown for as little as 4 days could be induced to express non-blood tissues.

Figure 6:
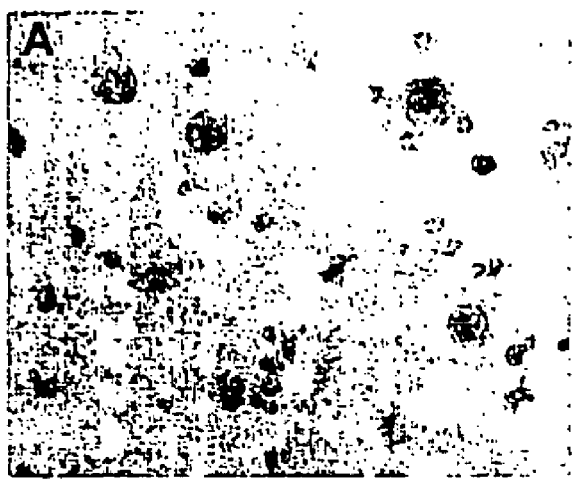
FIG. 6 shows osteoclast cells. $Lin^-$ cells grown in Fgf, SCF, FLT3 ligand for 4-28 days produced osteoclast cells as determined by A) TRAP positive staining and B) resorption of a calcium citrate substrate in the presence of serun and GM-CSF.
Figure 6:
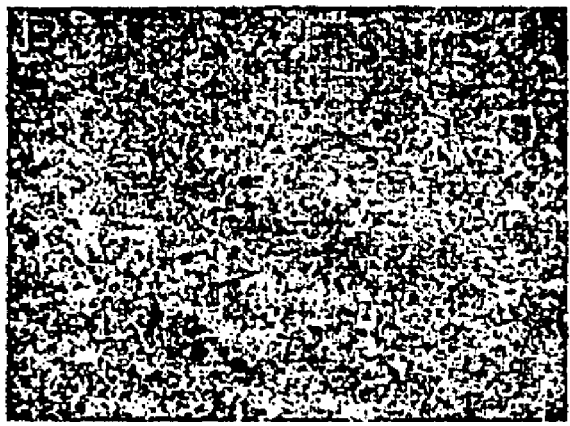

A) Osteoclast:

Days 0 cord blood stem cells were tested for markers for osteoclasts (TRAP). All samples tested were negative for this osteoclast marker. Cord blood stem cells (lineage minus) grown for 7, 14, 21 and 28 days in FGF-4, SCF, and FLT-3L are highly positive for TRAP (50% +), and multinucleated, both characteristics of osteoclasts (FIG. 6A). The maximum number of TRAP positive cells appeared at day 21 (80%) and leveled off to day 28. In order to measure functionality of the osteoclast-like cells, cells were placed on calcium citrate substrate and measured for absorbtion of the substrate. Cells grown in FGF, SCF, FLT3ligand were not functional osteoclasts despite being TRAP positive. The cells had to be placed into an osteoclast differentiation medium (serum containing medium with GM-CSF) in order to differentiate them into functional osteoclasts as observed by resorption of a calcium citrate substrate (FIG. 6B). Therefore, the culture conditions strongly induced osteoclast precursor production.

B) Osteoblast:

Differentiation cultures were used to produce osteoblast cells. Osteoblast cells have been produced from UCB Lin⁻ cells cultured with growth factors for at least 14 days [proliferation medium] and then placed in bone specific differentiation medium. The cells in the proliferation medium are negative for mature bone markers and morphology but have the capability to complete the differentiation program to give rise to mature bone cells with characteristics indicative of osteoblast cells. Prolonged culture periods with increased or decreased amounts of growth factors do not result in alkaline or mineralized cells. In. order to differentiate the osteoblasts into more mature bone cells the cells must be transferred to bone specific medium. Freshly isolated Lin– UCB cells placed into bone medium die without producing mature bone cells. These same cells cultured in Fgf, Scf, Flt3ligand medium for 7 days, then transferred to bone specific medium resulted in cells that are alkaline phosphatase positive. Furthermore, mineralization has been observed as the cells tested positive for Alizirin red staining.

Figure 7:
FIG. 7 shows Desmin positive cells. $Lin^-$ day 0 cells are negative for the early muscle marker, Desmin. $Lin^-$ cells grown for 7 days become desmin positive as determined by PCR These cells remain negative for mature muscle markers.
Figure 8:
FIG. 8 shows muscle actin (bottom panel) and Myo-D (top panel) positive cells. $Lin^-$ cells grown in Fgf, SCF, FLT3 ligand for 7 days then grown under conditions that support muscle cell growth resulted in cells positive for Muscle specific actin and Myo-D. Fewer cells are positive for the mature muscle marker Myo-D.
Figure 8:
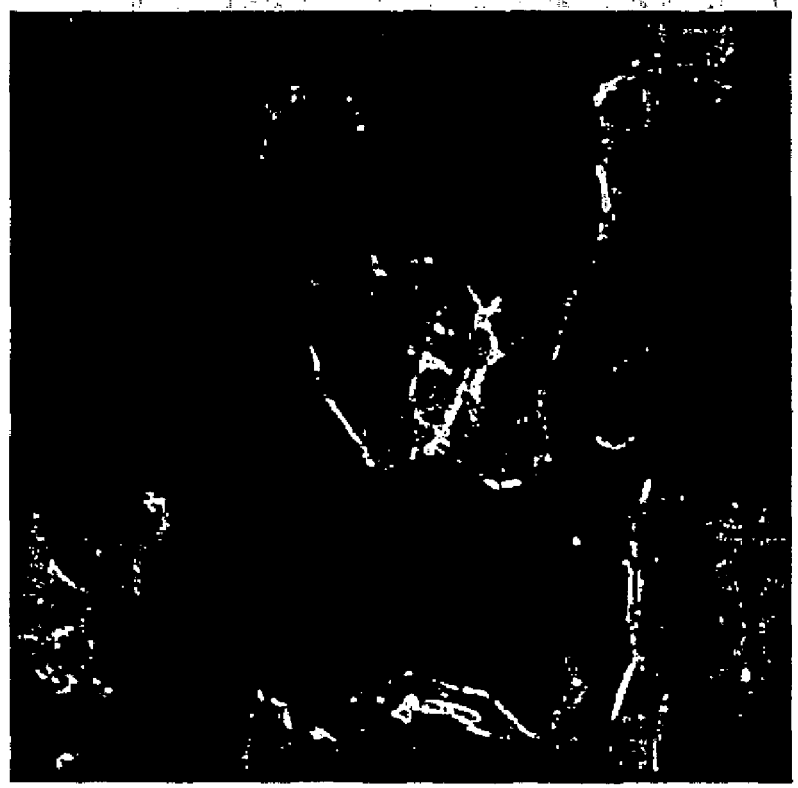

C) Muscle:

UCB lin⁻ cells were grown for 7 days in either FGF plus SCF, FLT-3L in serum free medium. The cells divided rapidly and maintained the round morphology of hematopoietic cells. At the end of the 8 day culture period, cells were tested for the embryonic/early muscle marker Desmin by RT-PCR A positive signal was achieved (FIG. 7). Cells were also tested for the mature muscle marker Myo-D, but remained negative. Cells that were grown in FGF placed into muscle specific cell culture media tested positive for myo-D and muscle specific actin by immunocytochemistry (FIG. 8).

D) Endothelial:

Flk-1 is a marker of mesoderm cells as well as hemangioblasts and endothelial cells. Endothelial precursors are FLK-1 positive and this marker is lost as these cells mature into functional endothelial cells. Day 0 cord blood stem cells are negative for flk-1. When placed into a 3D culture system, which allows for the production of vessels, all day 0 cells died. This is similar to the fate of the Lin⁻ UCB cells placed into other specialized mediums. This indicates that non-treated day Lin⁻ UCB cells do not have endothelial potential. When Lin–/UCB cells were grown in FGF-4, SCF, FLT-3L or TPO, SCF, FLT-3L for a minimum of 4 days and then placed in specialized endothelial cell cultures, the cells developed into endothelial cells.

UCB Lin⁻ cells were grown for 0, 7, 14, 21 and 28 days, and each cell population was placed into tissue culture conditions specific for the formation and support of endothelial cells. Two different cultures were used The first supports the growth of 3-D vessels. Cells were tested for the embryonic endothelial cell marker Flk-1 and for the mature endothelial marker CD31. There were no positive cells at day 0. The number of endothelial cells increased when cells were cultured for 7-28 days. FIG. 9A illustrates that the Flk-1 marker is present on the round immature cells and is lost as the cells take on the adherent, elongated endothelial morphology characteristic of endothelial cells. UCB Lin– cells grown in FGF, SCF, FLT-3L for at least 7 days were capable of forming small vessels in vitro (FIG. 9 B-F). Hypoxia can induce the production of VEGF, which induces the production of FLK-1 positive endothelial cells. Hypoxia plus FGF-4 gave the highest percentage of FLK-1 positive cells. Cells were harvested and stained for CD31 expression (FIG. 10). 80% of the cells in endothelial culture for a minimum of 14 days were CD31⁺. Interestingly, cells must be seeded at high density. After 7 days in cultures cells along the periphery elongate and move outward. After 4-6 weeks in culture a network of vessels is observed. The cells at the centre of the cell mass die off leaving an outer rim of vessels.

All of the experiments were repeated with cells sorted for FLK⁺ cells, CD34⁺ and CD45⁺. Only Flk1+ cells (+/– other markers) gave rise to endothelial cells.

E) Hepatocyte:

The ability of human UCB/Lin⁻ cells to produce functional liver cells was tested. The cells were tested in an in vivo model due to the lack of good in vitro hepatocyte models. UCB/Lin⁻ cells either untreated or grown in FGF for 7 days were injected via the tail vein into NOD/SCID mice. After 6-10 weeks the livers were isolated, and a single cell suspension was obtained. Mice that were positive for human blood cell engraftment had liver cells that were HLA-ABC$^{+/CD}$45⁻ suggesting the cells are human, non-blood cells (5/25). These cells were isolated by FACS sorting of single cell suspensions of the livers and tested for CYP1A2 expression. Of this sub group (2/5) few were positive for functional liver cells as assessed by CYP1A2 positive expression. The cells were stained with the anti-CD45 antibody, which is specific to human blood cells and anti-HLA-ABC, which is specific to all human cells. CD45 negative-HLA-ABC positive cells were identified in the mouse liver (FIG. 11A: arrow). Pre data suggests that the FGF-4 treated cells contributed 3 times as many cells as non-treated cells. This indirect approach allows identification of only cells in the liver that are human cells but not blood cells.

In order to identify functional human liver cells in the mice cells that were CYP1A2 positive were identified. CYP1A2 is an enzyme found in human liver tissue. It is only induced in mouse livers treated with dioxins, thus eliminating the possibility of cross-reaction with the antibody used in the assay. Furthermore the antibody used is specific to the human CYP1A2 and will not react with the murine CYP1A2 protein. NOD/SCID mice were not treated with any liver damaging chemicals (such as carbon tetra chloride) in order to maintain functionality of the newly engrafted cells. Furthermore, it was preferred that new cells infiltrate and take up residence in a liver that is not dramatically damaged. This allows assessment of the ability of UCB cells to be used in liver therapies for genetically defective livers where no physical damage may occur. This also provides a non-surgical method of treating inborn errors of metabolism. Therefore, only low levels of liver engraftment were expected About 10-20% of the CD45-/HLA-ABC+ cells detected in the mouse liver are also CYP1A2 positive. This suggest that although engraftment levels can be high, there are fewer functional hepatocytes (FIG. 11B, C). The same livers were sectioned and immunosistochemestry with CYP1A2 antibody detrected positive cells (FIG. 12).

Freshly isolated UCB cells (MNC or Lin⁻) were negative for CYP1A2. UCB/Lin⁻ cells that were treated with FSF for 7 days prior to tail vein injection into NOD/SCD mice were also negative for CYP1A2 expressing cells.

E) Astrocytes:

Due to the stromal nature of the cells, the cells were tested for the astrocytemarker Glial fibrillary acidic protein (GFAP). As for the above experiments, UCB Lin–cells were grown in serum free medium with growth factors for 0-7 days. The cells were then tested by PCR for the GFAP mRNA. Day 0 cells were negative, while cells grown for 7 days were positive (FIG. 13). Cells were also tested for GFAP protein expression by immunocytochemistry. Cells placed into medium supplemented with G-5 astrocyte growth supplement, used to promote astrocyte growth, were also positive for GFAP.

F) Neural:

Human UCB lin cells were grown in proliferation medium (Fgf, Scf, Flt3ligand) for 0-7 days and tested for the early neural marker NESTIN. UCB/Lin⁻ cells at day 0 tested negative for nestin. Once cells were grown for 7 days they became positive by PCR (FIG. 14). Since these cells were showing neural stem cell potential the cells were grown in various medium in order to induce the expression of mature neural markers as well as neural morphologies. It was expected that at some point the cells might take on a neural sphere morphology. In order to induce neural spheres the cells were grown in FGF/EGF/heparin/DMEM/F12HAMS medium, as published for the growth of neural stem cells (31), with and without serum. Day 0 and day 8 cells died after 3 days in the serum free medium, while cells survived in serum positive cultures they failed to form neural spheres. As for the experiments listed above, day zero cells in any of the neural cultures failed to express any neural markers. In order to express any neural markers or morphology the UCB/Lin⁻ cells had to first be grown in the proliferation medium described herein.

When day 7 UCB/Lin⁻ cells were placed into DMEM/10% serum cultures approximately 50% of the cells died while the remainder became elongated and adherent after 2-3 weeks in culture. These cells resembled a fibroblast morphology. Prolonged culture resulted in some cells (about 50%) of the adherent cells taking on a neural morphology. These cells were tested for the expression of neural filament protein, Parkin, nestin and Neural Specific Enolase. Cells with neural morphology were positive for at least one of each of these neural markers. Neurospheres, Parkin and Neuropositive cells are illustrated in FIG. 15.

Interestingly, selective growth/survival of neural cells resulted when 10 μm Retinoic Acid (RA) was added to cells grown in proliferation culture for 7 days then placed into DMEM/10% serum until adherent cells were present All other non-neural cells died as the RA containing cultures had more cell death present and half the number of cells versus the non-RA cultures after 7 days. Furthermore 90+% of the RA cells were positive for Neurofilament while only 50% of the non-RA were positive (FIG. 15). Cells in either medium survived for 12 weeks before cell division stops and the cells die. This is most likely due to the cells reaching a terminally differentiated state. If cells grown in proliferation medium for 7 days were placed directly into RA/DMEM/10% serum, cell clumping occurred. These cells remained alive, but do not resemble the tightly compacted neurospheres demonstrated previously (31). Cells could be maintained in RA cultures and the cells are positive for neurofilament In another experiment, the cells after 7 days of growth in Fgf, Scf, Flt3ligand were placed into cultures with Neural Growth Factor (NGF). In the presence of NGF and SCF and FLT-3 ligand the cells survive and some (<2%) neurofilament positive and Parlin positive cells were obtained. Thus NGF has the ability to convert cord blood stem cell into a neural stem cell. In contrast, NGF, SCF, Flt-3L cells were negative for the endothelial marker FLK-1 marker, as expected.

G) Adipocyte:

Mouse bone marrow derived stromal cells are capable of forming osteoclast and adipocyte cells in the same cultures. UCB Lin⁻ cells were placed in proliferation cultures and tested at the various days for adipocytes. Cells grown for 7-28 days were positive for adipocytes at low levels (<1%) when stained with SudanIV. Although less than 1% of the cells stained positive, this is significant as no cells were detected in the same cultures that lacked the growth factor GM-CSF (FIG. 16).

H) Single or Multiple Stem Cells:

Combined percentages of positive cells for at least one tissue-specific marker indicates that at minimum, single cells are expressing at least two unrelated markers. This suggests that one cell can give rise to two or more tissues. Growth of UCB/Lin⁻ cells in the proliferation medium for only 7 days results: in all cells being CD45$^{+/\ HLA\text{-}ABC}$+/CD33⁺, suggesting the presence of a single, multipotent, clonal population that is responsible for all observed cell types. In order to confirm this, single cells were placed into 96-well plates and grown in the proliferation medium. On average only 5/96 wells contained healthy dividing cells after 14 days of growth. Only one well continued to grow after 21 days and continued for 10 weeks in total before becoming quiescent and dying. The experiment was repeated with 10 cells per well 10/96 wells contained growing populations after 7 days.

Although specific tissues could not be tested for, the fact that 10% of 10 cells/well cultures had growth properties similar to our bulk culture, suggested that the starting population contains cells having different proliferation rates and survival rates but a single cell is responsible for the observed results. Multipotency may be dependent on cell-cell interaction and single cell plating may disrupt signalling pathways that are important to the survival of UCB multipotent cells.

Discussion:

A simple culture system is reported that allows for the production of multipotent stem cells derived from Umbilical Cord Blood. The availability of UCB and the ease of banking large numbers of samples will ensure the availability of HLA matched samples. Furthermore, the simplified culture system will allow for the expanded use of cord blood cells for tissue therapies beyond hematopoietic uses.

The mechanism by which the cells of the umbilical cord blood are capable of differentiating into non-hematopoietic cells could be due to: 1) the cells being naturally multipotent but their cell fate is determined by the surrounding cells or the local environment; or 2) the cell fate has been determined but the cells are reprogrammed when they are placed in an alternate environment (trans-differentiation).

Repopulating hematopoietic cells can be classified as progenitor cells ($CD34^+$, $CD38^{+/-}$ and $Lin^-$), which have limited renewal capacity, and stem cells ($CD34^{+/-}$, $CD38^-$, $Lin^-$), which are contained within the progenitor population and have a much greater capacity for self-renewal. In vitro expansion of progenitor cells can lead to their proliferation as measured by colony assays, or FACS analysis, but limited, if any, long term repopulation occurs during mouse bone marrow reconstitution studies (32). Furthermore, the autocrine reaction between stem cells, progenitor cells and accessory cells (all found within the UCB) makes it difficult to sort out whether any stem cell proliferation that does occur is due to the direct effect of exogenous cytokines or the indirect effect mediated by non-stem cells present in the aintial culture (33). Furthermore in vitro culture can result in the loss of specific cell surface markers resulting in combinations of surface molecules not found in the human body.

The methods of stem cell expansion of UCB, whether for hematopoietic or non-hematopoietic tissues, is the same. Treatment of the UCB cell population with any factor that stimulates the cell cycle leads to an increase in the number of stem cells, which can give rise to both hematopoietic and non-hematopoietic tissues/cells. The stem cells that give rise to non-hematopoietic tissues may be a rare population and a minimum growth period may be required in order for them to multiple to detectable levels. Alternatively, cell division may deregulate the hematopoietic stem cells increasing their stem cell potential so they develop characteristics similar to embryonic stem cells (ES cells). While not wishing to be bound to any theory, the data suggests the latter.

Studies using mouse bone marrow cells have demonstrated that these cells have the potential to become non-hematopoietic tissues. The ability of cells to trans-differentiate becomes a powerful tool for tissue therapy. It was illustrated herein that human umbilical cord blood stem cells can give rise, in vivo, and in vitro to some non-blood tissues. Here a 2-step culture system is reported. UCB cells can be induced to develop multipotent embryonic stem cell characteristics if placed into specialized proliferation medium, prior to exposure to specialized differentiation cultures (tissue specific). Freshly isolated UCB stem cells will not produce specialized cells. The cells have to be pre-cultured/grown in a proliferation culture in order to increase their tissue potential. The pre-culture acts to increase cell division, probably disrupting normal gene regulation resulting in a 'blank slate' phenotype. Cells grown for a minimum of one week are positive for a number of non-blood markers as detected by PCR, enzyme analysis, FACS or immunohistochemistry. Cells grown in proliferation medium are positive for embryonic or early non-blood tissue markers, such as the early muscle marker Desmin, but negative for the mature marker Myo-D. As shown for osteoclasts and endothelial cells, after growing in the proliferation medium for at least 7 days the cells can be further differentiated into mature and functional cell types by growing them in specialized, differentiation medium. These are identical characteristics to that of embryonic stem cells.

Growth Factors:

Growth Factors are involved either directly or indirectly in the proliferation, induction and patterning of tissue. Cell proliferation is controlled by extracellular signals (hormones, growth factors, and cytomines) during G1 phase of the cell cycle. The cells respond to these signals, both stimulatory and inhibitory by way of a distinct set of serine/threoninekinases, termed cdk for cyclin dependent kinases due to their association with short lived regulatory proteins referred to as cyclins. Four mammalian G1 cyclins have been characterized D1, D2, D3, and E. Each of the D cyclins is able to associate with one or more kinases cdk2, cdk4 and cdk 6 (34). Furthermore, the D cyclins seem unique as they respond directly to growth factor stimulation and less to normal endogenous cell cycle signals (35). The critical response period for the D cyclins is in G1, at START, as defined in yeast. Past this point the cell is no longer dependent on growth factors to continue the cell cycle (36).

Although the transition from G1 to S can be induced by various growth factors, stem cells whether neural or hematopoietic, reside mainly in Go, not G1 (37). CD34+ cells induced to enter G1 using cytokines were less likely to contribute to the repopulation cohort when compared to CD34+ cells treated with cytokines but remaining in Go (38). This result emphasizes the fact that entrance into the cell cycle can lead to differentiation. The addition of growth promoters (eg, FGF-4 or SCF (stem cell factor) & others) may prevent differentiation by keeping stem cells cycling. Additionally, both FGF and SCF have been implicated as direct blockers of apoptosis (39,40). Fibroblast growth factor (FGF), epidermal growth factor (EGF) and activin, are potent growth stimulators, which can alter D cyclin levels and promote proliferation (41, 42). Withdrawal of growth factors leads to reduced cyclin levels and differentiation. Thus, growth factors are regulators of proliferation and differentiation.

Cells will respond to a variety of cytokines and studies show that some have stronger mitogenic properties than others. In the Ladd et al., study (43) SCF, Flt3, I1-3 and IL-6 all have the capacity to stimulate cell proliferation but only IL-3 had the ability to maintain high proliferationrates. Other studies have indicated that specific cytokines such as SCF, although they are not strong mitogens, can prevent differentiation. SCF has the ability to increase CFU numbers alone or synergistically with other Growth factors. In vitro SCF is capable of maintaining a population (increased survival) of progenitors but did not cause cell proliferation. Used in combination with IL-3 or G-CSF, SCF had an additive effect on progenitor cell numbers over time (44). FLT3 ligand has been implicated in the maintenance of the CD34 positive cell population in the presence of the strong mitogenic activity of IL-3 (45). In contrast to SCF or FLT-3 ligand, it is clear that other factors such as BMP4, retinoic acid or TGF-β are strong differentiation factors. The TGF-β family member, BMP, is important as inducers of cell differentiation. In the mouse embryo, BMP's are important in the initiation of neural differentiation. Although the mechanism is not clearly understood, BMP's have a negative effect on the cell cycle resulting in longer cell cycle times and increased gene activation resulting in differentiation. For example, BMP-6 induces mesenchymal cells to differentiate into osteoblasts and in bone marrow, BMP-6 reduces the stromal derived levels of IL-6 (46). IL-3 causes an increase in overall cell numbers but a decrease in stem/progenitor cells as measured by CD34 surface markers, TNFα causes a decrease in the number of LTC-IC's (47) and TGF-β reduces mouse BM engraftment (48). Although IL-3 in some conditions has a positive effect on progenitor cell proliferation, IL-3 may inhibit the ability of HSC to home to the bone marrow. Thus an increase in cell numbers in vitro is not accompanied by an increase in bone marrow engraftment (49).

Conclusion:

A proliferation system is described that allows for the development and subsequent expansion of a human umbilical cord derived stem cell that has the ability to give rise to hematopoietic and non-hematopoietic tissues.

EXAMPLE 2

Hematopoietic Stem Cell Expansion:

The experiments discussed in this Example were designed to produce more hematopoietic tissues from a single UCB sample in order to obtain enough cells to carry out successful bone marrow transplants on single adults or multiple adult patients. It is important to eliminate both the requirement for serum and conditioned medium as this is not feasible for a clinical setting. Furthermore, reducing the dependence on serum and conditioned medium provides more control over maintenance of stem cell phenotype and cell proliferation. To this end the ability of various growth factors to maintain UCB-HSC in the presence of conditioned medium from a human embryonic fibroblast cell line (CM-HEF) were tested. Cells were then tested in serum free/conditioned medium free media Stem cell maintenance and proliferation was tested using colony forming unit (CFU) assays and cell surface marker analysis as an initial indicator of stem cell proliferation (FIG. 17) In subsequent experiments, LTC-IC and NOD/SCID assays were used to verify stem cell phenotype and the ability of these cells to engraft (FIG. 5).

The serum free conditioned medium plus FGF-4 aided cell proliferation but was not as proficient as serum+conditioned medium+FGF4. Cultures were also set up where the conditioned medium was eliminated, using medium with 10% serum and FGF-4. Two mediums (DMEM and IMDM) were tested. The addition of SCE to the FGF-4containing medium increased the proliferation rate. The serum was removed from the conditioned medium by replacing both with a combination of TPO, or FGF-4+/−IL-3, SCF, FLT-3 ligand. Note that IL-3 may affect stem cell homing to the bone marrow.

Equivalent stem cell expansion results were obtained using non-conditioned, serum free IMDA with the addition of 25 ng/ml each of TPO or FGF-4, +[SCF, and FLT-3 ligand] to that of serum+conditioned medium. Feedings of 2-3 times per week are required to maintain high proliferation levels and maintenance of the stem cell phenotype. Addition of 100 ng/ml of each growth factor at the same frequency did not have an effect.

Using the above serum free/conditioned medium-free media resulted in an increase in CFU's and LTC-IC over the first 8 days over day 0 cells as anaylzed by LTC-IC, flow cytometry for CD34+/CD38-cells, Lineage depletion (Lin−), and NOD/SCID mouse studies. Although overall cell numbers increased when cells were allowed to grow for an additional 8 days (day 8-16) the hematopoietic stem cell population was depleted.

While the present invention has been described with reference to what is presently considered to be a preferred embodiment, it is to be understood that the invention is not limited to the disclosed embodiment. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

LIST OF REFERENCES

1. Rubenstein et al, 1998, N Engl. J. Med. 339, 1565-77
2. Sambrook, Fritsch, & Maniatis, Molecular Cloning: A Laboratory Manual, Second Edition (1989) Cold Spring Harbor Laboratory Press, Cold Spring Harbor, N.Y.)
3. DNA Cloning: A Practical Approach, Volumes I and II (D. N. Glover ed. 1985);
4. Oligonucleotide Synthesis (M. J. Gait ed. 1984);
5. Nucleic Acid Hybridization B. D. Hames & S. J. Higgins eds. (1985);
6. Transcription and Translation B. D. Hames & S. J. Higgins eds (1984);
7. Animal Cell Culture R. I. Preshney, ed. (1986);
8. Immobilized Cells and enzymes IRL Press, (1986); and
9. B. Perbal, A Practical Guide to Molecular Cloning (1984).
10. Stites et al. (eds)Basic and Clinical Immunology, 8$^{th}$ Ed, Appleton & Lange, Norwalk, Conn. (1994);
11. Mishell and Shigi (eds), Selected Methods in Cellular Immunology, W. H. Freeman and Co., New York (1980).
12. Givol and Yayon, 1992, FASEB J., 6:33622269
13. Dionne et al., 1990, EMBO J., 9:2685-2692
14. Ornitz and Leder, 1992, J. Biol. Chem., 267:16305-16311
15. Chellaiah et al., 1994, J. Biol. Chem., 269(15):11620-11622,
16. Small et al., 1994, Proc. Natl. Acad. Sci. 91:459-463
17. Buhring et al. in Schlossman et al, (Eds), Leucocyte Typing V, Oxford University Press, Oxford 1995, pp. 1882-1888)
18. Zsebo et al., 1990, Cell 63:213-224,
19. Gluckman et al, 1993, N Engl J Med 337, 373-81
20. Van der Putten, 1985, Proc Natl Acad Sci U S A.;82:6148-52;
21. Stewart et al. 1987, EMBO J. 6:383-388).
22. Heim et al, 1994, Proc. Natl. Acad. Sci. 91:12501,
23. M. Zernicka-Goetz et al, 1997, Development 124:1133-1137,
24. Okabe, M. et al, FEBS Letters 407:313-319, 1997;
25. D. P. Hill and W. Wurst, 1993, Methods in Enzymology, 225:664
26. Dick J E, Ann N Y Acad Sci. 1999 Apr. 30;872:211-7

27. Tropepe V, et al, 2000, Science 287, pp. 2032)
28. Minkin Cedric, "Bone Acid Phosphatase: Tartrate-resistant acid phosphatase as a Marker of Osteoclast Function", Calcif Tissuse Int (1982) 34:285-290.
29. Jiang et al, 2002, Nature 418, 41-49
30. Quirici, et al, 2002, Experimental Haematology 30, 783-791
31. Tropepe et al., Dev Biol 1999 Apr. 1;208(1):166-88)
32. Piacibello et al, 1999, Blood 93, 3736-49
33. Madlambayan et al., 2001, J Hematother Stem Cell Res. 10, 481-492
34. Sicinski et al, 1995. Cell, 82, 621-30
35. Matsushilne et al, 1991, Cell 65, 701-713
36. Merrill et al., 1992, BioEssay 14, 823-830
37. Ogawa, M. 1993, Blood 81, 2844-2853
38. Gothot et al., 1998, Blood 92, 2641-2649
39. Huang et al, 1999, Blood 93,2569-2577
40. Gruber et al., 1999, Blood 94, 1077-85
41. Sherr 1992, Ciba Found Symp, 170, 209-219
42. Rao and Kohtz, 1995, J. Biol. Chem, 270, 4093-4100
43. Ladd et al., 1997, Blood 90, 658-68
44. Li C, Johnson G, Blood 84; 1994; 408-414
45. Nielsen, J. Hemato stem cell res 2000, 9(5):695-701).
46. Ahmed N, et al 2000, Exp. Hematology 28:1495).
47. Petzer et al., 1996, J Exp Med, 183, 2551-2558
48. Gao et al 1998, PNAS 95, 13006-13011
49. Yonemura et al, 1996, PNAS 93:4040
50. C. Basilico and D. Moscatelli, Adv. Cancer Re. 59, 115 (1992)
51. Moroni E, Dell'Era P, Rusnati M, Presta M. J. Hematother Stem Cell Res 2002 Feb.;11(1):19-32
52. Goldfarb M. Sci STKE 2001 Oct. 30;2001(106):PE37
53. Gilliland D G and Griffin J D. Blood 2002 Sep. 1;100(5): 1532-42
54. Smith M A, Court E L, Smith J G Blood Rev 2001 Dec.;15(4):191-7

We claim:

1. A method for producing a cellular composition comprising multipotent cells that express CD45, HLA-ABC and Oct-4 and can differentiate into endothelial cells, said method comprising:
   (a) enriching hematopoietic cells using negative selection to obtain a hematopoietic cell preparation enriched for $CD45^+HLA\text{-}ABC^+$ cells; and
   (b) culturing the hematopoietic cell preparation enriched for $CD45^+HLA\text{-}ABC^+$ cells in a medium comprising FGF-4, SCF and Flt-3 ligand to provide said multipotent cells.

2. The method as claimed in claim 1, wherein the hematopoietic cells are obtained from a source selected from the group consisting of blood, blood fractions, umbilical cord blood, and bone marrow.

3. The method as claimed in claim 1, wherein the hematopoietic cell preparation is enriched in $CD45^+HLA\text{-}ABC^{+-}CD2^-CD3^{31}CD14^{31}\ CD16^-CD19^-CD24^-CD56^-CD66^-$ glycophorin $A^-$ cells.

4. A cellular composition produced by the method of claim 1.

5. The cellular composition as claimed in claim 4, wherein the multipotent cells in the cellular composition express the early endothelial marker CD31.

6. A pharmaceutical composition comprising a cellular composition of claim 4, and a pharmaceutically acceptable carrier, excipient, or diluent.

7. The method as claimed in claim 3, wherein the hematopoietic cell preparation is enriched in at least 70% $CD45^+HLA\text{-}ABC^{+-}CD2^-CD3^-CD14^-CD16^-CD19^-CD24^-CD56^-CD66^-$ glycophorin $A^-$ cells.

* * * * *

UNITED STATES PATENT AND TRADEMARK OFFICE
CERTIFICATE OF CORRECTION

PATENT NO. : 7,625,752 B2  Page 1 of 1
APPLICATION NO. : 10/499849
DATED : December 1, 2009
INVENTOR(S) : Robert Casper and Ian Rogers It is certified that error appears in the above-identified patent and that said Letters Patent is hereby corrected as shown below:

Column 44, lines 20-22, replace "$CD45^+HLA\text{-}ABC^{+-}CD2^-CD3^{31}CD14^{31}\ CD16^-$ $CD19^-CD24^-CD56^-CD66^-$ glycophorin $A^-$ cells" with -- $CD45^+HLA\text{-}ABC^+CD2^-CD3^-$ $CD14^-CD16^-CD19^-CD24^-CD56^-CD66^-$ glycophorin $A^-$ cells --.

Column 44, lines 32-34, replace "$CD45^+HLA\text{-}ABC^{+-}CD2^-CD3^-CD14^-CD16^-CD19^-$ $CD24^-CD56^-CD66^-$ glycophorin $A^-$ cells" with -- $CD45^+HLA\text{-}ABC^+CD2^-CD3^-CD14^-$ $CD16^-CD19^-CD24^-CD56^-CD66^-$ glycophorin $A^-$ cells --.

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,625,752 B2  Page 1 of 1
APPLICATION NO. : 10/499849
DATED : December 1, 2009
INVENTOR(S) : Casper et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 769 days.

Signed and Sealed this

Second Day of November, 2010

David J. Kappos
*Director of the United States Patent and Trademark Office*